United States Patent
Zheng et al.

(10) Patent No.: US 12,371,493 B2
(45) Date of Patent: *Jul. 29, 2025

(54) MONOCLONAL ANTIBODY AGAINST HUMAN LAG-3, METHOD FOR PREPARING THE SAME, AND USE THEREOF

(71) Applicant: WUXI BIOLOGICS (SHANGHAI) CO., LTD., Shanghai (CN)

(72) Inventors: Yong Zheng, Shanghai (CN); Qiong Wu, Shanghai (CN); Jing Li, Shanghai (CN)

(73) Assignee: WUXI BIOLOGICS (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/472,144

(22) Filed: Sep. 21, 2023

(65) Prior Publication Data

US 2024/0067725 A1    Feb. 29, 2024

Related U.S. Application Data

(63) Continuation of application No. 16/976,404, filed as application No. PCT/CN2019/076356 on Feb. 27, 2019, now Pat. No. 11,795,221.

(30) Foreign Application Priority Data

Feb. 28, 2018  (WO) ................ PCT/CN2018/077588
May 18, 2018  (WO) ................ PCT/CN2018/087504

(51) Int. Cl.
| | |
|---|---|
| A61K 39/00 | (2006.01) |
| A61K 39/395 | (2006.01) |
| C07H 21/04 | (2006.01) |
| C07K 16/00 | (2006.01) |
| C07K 16/28 | (2006.01) |
| C07K 16/46 | (2006.01) |
| C12N 15/00 | (2006.01) |
| G01N 33/53 | (2006.01) |
| G01N 33/574 | (2006.01) |

(52) U.S. Cl.
CPC ... *C07K 16/2803* (2013.01); *G01N 33/57492* (2013.01); *A61K 2039/505* (2013.01); *C07K 2317/21* (2013.01); *C07K 2317/33* (2013.01); *C07K 2317/56* (2013.01); *C07K 2317/565* (2013.01); *C07K 2317/732* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 10,259,874 B2 | 4/2019 | Wang et al. | |
| 11,661,452 B2 * | 5/2023 | Chen ............... | A61P 35/00 |
| | | | 424/172.1 |
| 11,795,221 B2 * | 10/2023 | Zheng ............. | G01N 33/57492 |
| 2011/0150892 A1 | 6/2011 | Thudium et al. | |
| 2012/0058122 A1 | 3/2012 | Rothe et al. | |
| 2017/0101472 A1 | 4/2017 | Ullman et al. | |
| 2017/0137514 A1 | 5/2017 | Lonberg et al. | |
| 2017/0306016 A1 | 10/2017 | Wang et al. | |
| 2022/0056126 A1 | 2/2022 | Grandal et al. | |

FOREIGN PATENT DOCUMENTS

| | | |
|---|---|---|
| CN | 101326196 A | 12/2008 |
| CN | 102174105 A | 9/2011 |
| CN | 102666589 A | 9/2012 |
| CN | 104411723 A | 3/2015 |
| CN | 106336460 A | 1/2017 |
| CN | 107405397 A | 11/2017 |
| CN | 107530420 A | 1/2018 |
| NZ | 579734 A | 1/2012 |
| WO | WO 2007/056470 A2 | 5/2007 |
| WO | WO 2011/053465 A1 | 5/2011 |
| WO | WO 2015/138920 A1 | 9/2015 |
| WO | WO 2016/068803 A1 | 5/2016 |
| WO | WO 2017/220569 A1 | 12/2017 |

(Continued)

OTHER PUBLICATIONS

Brown et al., "Tolerance to Single, but Not Multiple, Amino Acid Replacements in Antibody VH CDR2: A Means of Minimizing B Cell Wastage from Somatic Hypermutation?", J. Immunol., 1996, 156: 3285-3291.

Vajdos et al., "Comprehensive Functional Maps of the Antigen-binding Site of an Anti-ErbB2 Antibody Obtained with Shotgun Scanning Mutagenesis", J. Mol. Biol., 2002, 320: 415-428.

Padlan, "Anatomy of the Antibody Molecule", Molecular Immunology, 1994, 31(3): 169-217.

Rabia et al., "Understanding and overcoming trade-offs between antibody affinity, specificity, stability and solubility", Biochemical Engineering Journal, 2018, 137: 365-374.

(Continued)

*Primary Examiner* — Maher M Haddad
(74) *Attorney, Agent, or Firm* — James S. Keddie; Bozicevic, Field & Francis LLP

(57) ABSTRACT

Provided are novel fully human monoclonal antibodies that bind to human LAG-3. It also provides the methods of hybridoma generation using humanized rats, the nucleic acid molecules encoding the anti-LAG-3 antibodies, expression vectors and host cells used for the expression of anti-LAG-3 antibodies. The invention further provides the methods for validating the function of antibodies in vitro. The antibodies of invention provide a potent agent for the treatment of multiple cancers via modulating human immune function.

18 Claims, 10 Drawing Sheets

Specification includes a Sequence Listing.

(56) References Cited

FOREIGN PATENT DOCUMENTS

WO     WO 2018/034227 A1     2/2018

OTHER PUBLICATIONS

Ascierto, P. A. et al. (2017) "Efficacy of BMS-986016, A Monoclonal Antibody That Targets Lymphocyte Activation Gene-3 (LAG-3), In Combination With Nivolumab in Pts With Melanoma Who Progressed During Prior Anti-PD-1/PD-L1 Therapy (Mel Prior IO) In All-Comer And Biomarker-Enriched Populations," Annals Of Oncology 28:v605.

Extended European Search Report mailed on Oct. 20, 2021 for EP Application No. 19 760 533.0, filed on Feb. 27, 2019, 12 pages.

International Search Report mailed on May 31, 2019, for PCT Application No. PCT/CN2019/076356, filed on Feb. 27, 2019, 10 pages.

Written Opinion of the International Searching Authority mailed on May 31, 2019, for PCT Application No. PCT/CN2019/076356, filed on Feb. 27, 2019, 5 pages.

Woo et al., "Immune Inhibitory Molecules LAG-3 and PD-1 Synergistically Regulate T-cell Function to Promote Tumoral Immune Escape", Cancer Research, 2012, 72(4): 917-927.

Caldas et al., "Humanization of the anti-CD18 antibody 6.7: an unexpected effect of a framework residue in binding to antigen", Molecular Immunology, 2003, 39: 941-952.

Du et al., "Molecular Basis of Recognition of Human Osteopontin by 23C3, a Potential Therapeutic Antibody for Treatment of Rheumatoid Arthritis", J. Mol. Biol., 2008, 382: 835-842.

Kunik et al., "Structural Consensus among Antibodies Defines the Antigen Binding Site", PLoS Computational Biology, 2012, 8(2): e1002388, 12 pages.

Andrews et al., "LAG3 (CD223) as a Cancer Immunotherapy Target", Immunol Rev., Mar. 2017, 276(1): 80-96.

HE et al., "The Research Progress of LAG-3 Molecular", Progress in Modern Biomedicine, May 2014, 14(15): 2989-2993.

First Examination Report Notification issued for Chinese Application No. 202210735906.2, mailed on Dec. 31, 2024.

\* cited by examiner

SEQUENCE LISTING

```
Sequence total quantity: 28
SEQ ID NO: 1                moltype = AA  length = 10
FEATURE                     Location/Qualifiers
REGION                      1..10
                            note = CDRH1 of 1.53.3-uAb-IgG4k
source                      1..10
                            mol_type = protein
                            organism = synthetic construct
SEQUENCE: 1
GGSFSGYYWS                                                                 10

SEQ ID NO: 2                moltype = AA  length = 16
FEATURE                     Location/Qualifiers
REGION                      1..16
                            note = CDRH2 of 1.53.3-uAb-IgG4k
source                      1..16
                            mol_type = protein
                            organism = synthetic construct
SEQUENCE: 2
EINHRGNTNY NPSLKS                                                          16

SEQ ID NO: 3                moltype = AA  length = 13
FEATURE                     Location/Qualifiers
REGION                      1..13
                            note = CDRH3 of 1.53.3-uAb-IgG4k
source                      1..13
                            mol_type = protein
                            organism = synthetic construct
SEQUENCE: 3
GEDYSDYDYY GDF                                                             13

SEQ ID NO: 4                moltype = AA  length = 11
FEATURE                     Location/Qualifiers
REGION                      1..11
                            note = CDRL1 of 1.53.3-uAb-IgG4k
source                      1..11
                            mol_type = protein
                            organism = synthetic construct
SEQUENCE: 4
RASQSISSYL A                                                               11

SEQ ID NO: 5                moltype = AA  length = 7
FEATURE                     Location/Qualifiers
REGION                      1..7
                            note = CDRL2 of 1.53.3-uAb-IgG4k
source                      1..7
                            mol_type = protein
                            organism = synthetic construct
SEQUENCE: 5
AASNRAT                                                                    7

SEQ ID NO: 6                moltype = AA  length = 9
FEATURE                     Location/Qualifiers
REGION                      1..9
                            note = CDRL3 of 1.53.3-uAb-IgG4k
source                      1..9
                            mol_type = protein
                            organism = synthetic construct
SEQUENCE: 6
QQRSNWPLT                                                                  9

SEQ ID NO: 7                moltype = AA  length = 12
FEATURE                     Location/Qualifiers
REGION                      1..12
                            note = CDRH1 of 3.40.19-uAb-IgG4L
source                      1..12
                            mol_type = protein
                            organism = synthetic construct
SEQUENCE: 7
GDSISSTSYY WG                                                              12

SEQ ID NO: 8                moltype = AA  length = 16
FEATURE                     Location/Qualifiers
REGION                      1..16
                            note = CDRH2 of 3.40.19-uAb-IgG4L
source                      1..16
                            mol_type = protein
                            organism = synthetic construct
```

```
SEQUENCE: 8
SFYYSGSTYY NPSLKS                                                          16

SEQ ID NO: 9              moltype = AA  length = 10
FEATURE                   Location/Qualifiers
REGION                    1..10
                          note = CDRH3 of 3.40.19-uAb-IgG4L
source                    1..10
                          mol_type = protein
                          organism = synthetic construct
SEQUENCE: 9
MQLWSYDVDV                                                                 10

SEQ ID NO: 10             moltype = AA  length = 14
FEATURE                   Location/Qualifiers
REGION                    1..14
                          note = CDRL1 of 3.40.19-uAb-IgG4L
source                    1..14
                          mol_type = protein
                          organism = synthetic construct
SEQUENCE: 10
TGTSSDVGGY DYVA                                                            14

SEQ ID NO: 11             moltype = AA  length = 7
FEATURE                   Location/Qualifiers
REGION                    1..7
                          note = CDRL2 of 3.40.19-uAb-IgG4L
source                    1..7
                          mol_type = protein
                          organism = synthetic construct
SEQUENCE: 11
DVSERPS                                                                     7

SEQ ID NO: 12             moltype = AA  length = 11
FEATURE                   Location/Qualifiers
REGION                    1..11
                          note = CDRL3 of 3.40.19-uAb-IgG4L
source                    1..11
                          mol_type = protein
                          organism = synthetic construct
SEQUENCE: 12
SSYTSTTTLV V                                                               11

SEQ ID NO: 13             moltype = AA  length = 121
FEATURE                   Location/Qualifiers
REGION                    1..121
                          note = VH of 1.53.3-uAb-IgG4k
source                    1..121
                          mol_type = protein
                          organism = synthetic construct
SEQUENCE: 13
QVQLQQWGAG LLKPSETLSL TCGVYGGSFS GYYWSWIRQP PGMGLEWIGE INHRGNTNYN          60
PSLKSRVTIS EDTSKNQFSL RLSSVTAADT AVYFCTRGED YSDYDYYGDF WGQGTLVTVS         120
S                                                                        121

SEQ ID NO: 14             moltype = AA  length = 107
FEATURE                   Location/Qualifiers
REGION                    1..107
                          note = VL of 1.53.3-uAb-IgG4k
source                    1..107
                          mol_type = protein
                          organism = synthetic construct
SEQUENCE: 14
EIVLTQSPAT LSLSQGERAT LSCRASQSIS SYLAWYQQKP GQAPRLLIYA ASNRATGIPA          60
RFSGSGSGTD FTLTISSLEP EDFAIYYCQQ RSNWPLTFGG GTKVEIK                      107

SEQ ID NO: 15             moltype = AA  length = 120
FEATURE                   Location/Qualifiers
REGION                    1..120
                          note = VH of 3.40.19-uAb-IgG4L
source                    1..120
                          mol_type = protein
                          organism = synthetic construct
SEQUENCE: 15
QLQLQESGPG LVKPSETLSL TCTVSGDSIS STSYYWGWIR QPPGKGLEWI GSFYYSGSTY          60
YNPSLKSRVT ISVDTSKNQF SLKLNSVTAA DTAVYYCARM QLWSYDVDVW GQGTTVTVSS         120

SEQ ID NO: 16             moltype = AA  length = 111
FEATURE                   Location/Qualifiers
```

| | | |
|---|---|---|
| REGION | 1..111 | |
| | note = VL of 3.40.19-uAb-IgG4L | |
| source | 1..111 | |
| | mol_type = protein | |
| | organism = synthetic construct | |

SEQUENCE: 16

```
QSALTQPASV SGSPGQSITI SCTGTSSDVG GYDYVAWYQQ HPGKVPKLMI YDVSERPSGV    60
SNRFSGSKSG NTASLTISGL QAEDEADYYC SSYTSTTTLV VFGGGTKLSV L             111
```

| | | |
|---|---|---|
| SEQ ID NO: 17 | moltype = DNA  length = 363 | |
| FEATURE | Location/Qualifiers | |
| misc_feature | 1..363 | |
| | note = VH of 1.53.3-uAb-IgG4k | |
| source | 1..363 | |
| | mol_type = other DNA | |
| | organism = synthetic construct | |

SEQUENCE: 17

```
caggtgcagc tacagcagtg gggcgcagga cttttgaagc cttcggagac cctgtccctc    60
acctgcggtg tctatggtgg gtccttcagt ggttactact ggagctggat ccgccagccc   120
ccagggatgg ggctggagtg gattggggaa atcaatcatc gtggaaacac caactacaac   180
ccgtccctca agagtcgcgt caccatatca gaagacacgt ccaagaacca gttccccctg   240
aggctgagct ctgtgaccgc cgcggacacg gctgtgtatt tctgtacgag aggagaggac   300
tatagtgact acgattacta tggggacttc tggggccagg gaacccctgt caccgtctcc   360
tca                                                                  363
```

| | | |
|---|---|---|
| SEQ ID NO: 18 | moltype = DNA  length = 321 | |
| FEATURE | Location/Qualifiers | |
| misc_feature | 1..321 | |
| | note = VL of 1.53.3-uAb-IgG4k | |
| source | 1..321 | |
| | mol_type = other DNA | |
| | organism = synthetic construct | |

SEQUENCE: 18

```
gaaattgtgt tgacacagtc tccagccacc ctgtctttgt ctcaaggggg aagagccacc    60
ctctcctgca gggccagtca gagtattagc agctacttag cctggtacca acagaaacct   120
ggccaggctc ccaggctcct catctatgct gcatccaaca gggccactgg catcccagcc   180
aggttcagtg gcagtgggtc tgggacagac ttcactctca ccatcagcag cctagagcct   240
gaagattttg caatttatta ctgtcagcag cgtagcaact ggcctctcac tttcggcgga   300
gggaccaagg tggagatcaa a                                              321
```

| | | |
|---|---|---|
| SEQ ID NO: 19 | moltype = DNA  length = 360 | |
| FEATURE | Location/Qualifiers | |
| misc_feature | 1..360 | |
| | note = VH of 3.40.19-uAb-IgG4L | |
| source | 1..360 | |
| | mol_type = other DNA | |
| | organism = synthetic construct | |

SEQUENCE: 19

```
cagctgcagc tgcaggagtc gggcccagga ctggtgaagc cttcggagac cctgtccctc    60
acctgcactg tctctggtga ctccatcagc agtactagtt actactgggg ctggatccgc   120
cagccccag ggaaggggct ggagtggatt gggagtttct attatagtgg gagcacctac    180
tacaacccgt ccctcaagag tcgagtcacc atttccgtag acacgtccaa gaaccagttc   240
tccctgaagc tgaactctgt gaccgccgca gacacggctg tgtattactg tgcgaggatg   300
cagtctatggt cgtacgatgt ggacgtctgg ggccaaggga ccacggtcac cgtctcctca   360
```

| | | |
|---|---|---|
| SEQ ID NO: 20 | moltype = DNA  length = 333 | |
| FEATURE | Location/Qualifiers | |
| misc_feature | 1..333 | |
| | note = VL of 3.40.19-uAb-IgG4L | |
| source | 1..333 | |
| | mol_type = other DNA | |
| | organism = synthetic construct | |

SEQUENCE: 20

```
cagtctgccc tgactcaacc tgcctccgtg tctgggtctc ctggacagtc gatcaccatc    60
tcctgcactg gaaccagcag tgacgttggt gggtatgact atgtcgcctg gtaccaacaa   120
cacccaggca aagtccccaa actcatgatt tatgatgtca gtgagcggcc ctcaggggtt   180
tctaatcgct tctctggctc caagtctggc aacacggcct ccctgaccat ctctgggctc   240
caggctgagg acgaggctga ttattactgc agctcatata caagcaccac cactctcgtt   300
gtgttcggcg gagggaccaa gctgtccgtc ctg                                 333
```

| | | |
|---|---|---|
| SEQ ID NO: 21 | moltype = AA  length = 421 | |
| FEATURE | Location/Qualifiers | |
| REGION | 1..421 | |
| | note = human LAG-3 ECD | |
| source | 1..421 | |
| | mol_type = protein | |
| | organism = synthetic construct | |

SEQUENCE: 21

```
PVVWAQEGAP AQLPCSPTIP LQDLSLLRRA GVTWQHQPDS GPPAAAPGHP LAPGPHPAAP    60
```

```
SSWGPRPRRY TVLSVGPGGL RSGRLPLQPR VQLDERGRQR GDFSLWLRPA RRADAGEYRA    120
AVHLRDRALS CRLRLRLGQA SMTASPPGSL RASDWVILNC SFSRPDRPAS VHWFRNRGQG    180
RVPVRESPHH HLAESFLFLP QVSPMDSGPW GCILTYRDGF NVSIMYNLTV LGLEPPTPLT    240
VYAGAGSRVG LPCRLPAGVG TRSFLTAKWT PPGGGPDLLV TGDNGDFTLR LEDVSQAQAG    300
TYTCHIHLQE QQLNATVTLA IITVTPKSFG SPGSLGKLLC EVTPVSGQER FVWSSLDTPS    360
QRSFSGPWLE AQEAQLLSQP WQCQLYQGER LLGAAVYFTE LSSPGAQRSG RAPGALPAGH    420
L                                                                   421

SEQ ID NO: 22           moltype = DNA  length = 1263
FEATURE                 Location/Qualifiers
misc_feature            1..1263
                        note = human LAG-3 ECD
source                  1..1263
                        mol_type = other DNA
                        organism = synthetic construct
SEQUENCE: 22
ccggtggtgt gggcccagga gggggctcct gcccagctcc cctgcagccc cacaatcccc    60
ctccaggatc tcagccttct gcgaagagca ggggtcactg gcagcatca gccagacagt    120
ggcccgcccg ctgccgcccc cggccatccc ctggcccccg ccctcaccc ggcggcgccc     180
tcctcctggg ggcccaggcc ccgccgctac acggtgctga gcgtgggtcc cggaggcctg    240
cgcagcggga ggctgcccct gcagcccgc gtccagctgg atgagcgcgg ccggcagcgc     300
ggggacttct cgctatggct gcgcccagcc cggcgcggg acgccggcga gtaccgccgc     360
gcggtgcacc tcagggaccg cgccctctcc tgccgcctcc gtctgcgcct gggccaggcc    420
tcgatgactg ccagccccc aggatctctc agagcctccg actgggtcat tttgaactgc     480
tccttcagcc gccctgaccg cccagcctct gtgcattggt tccggaaccg gggccagggc    540
cgagtccctg tccggagtc cccccatcac cacttagccg aaagcttcct cttcctgccc    600
caagtcagcc ccatggactc tgggcccgg gctgcatcc tcacctacag agatggcttc      660
aacgtctcca tcatgtataa cctcactgtt ctgggtctgg agcccccaac tcccttgaca    720
gtgtacgctg gagcaggttc cagggtgggg ctgccctgcc gctgcctgc tggtgtgggg    780
acccgcttct tcctcactgc caagtggact cctcctgggg gaggccctga cctcctggtg    840
actggagaca atggcgactt tacccttcga ctagaggatg tgagccaggc ccaggctggg    900
acctacacct gccatatcca tctgcaggaa cagcagctca atgccactgt cacattggca    960
atcatcacag tgactcccaa atcctttggg tcacctggat ccctgggaaa gctgctttgt   1020
gaggtgactc cagtatctgg acaagaacgc tttgtgtgga gctctctgga cacccatcc    1080
cagaggagtt tctcaggacc ttggctggag gcacaggagg cccagctcct ttcccagcct   1140
tggcaatgcc agctgtacca gggggagagg cttcttggag cagcagtgta cttcacagag   1200
ctgtctagcc caggtgccca acgctctggg agagcccag gtgccctccc agcaggccac    1260
ctc                                                                1263

SEQ ID NO: 23           moltype = AA  length = 525
FEATURE                 Location/Qualifiers
REGION                  1..525
                        note = full-length human LAG-3
source                  1..525
                        mol_type = protein
                        organism = synthetic construct
SEQUENCE: 23
MWEAQFLGLL FLQPLWVAPV KPLQPGAEVP VVWAQEGAPA QLPCSPTIPL QDLSLLRRAG     60
VTWQHQPDSG PPAAAPGHPL APGPHPAAPS SWGPRPRRYT VLSVGPGGLR SGRLPLQPRV    120
QLDERGRQRG DFSLWLRPAR RADAGEYRAA VHLRDRALSC RLRLRLGQAS MTASPPGSLR    180
ASDWVILNCS FSRPDRPASV HWFRNRGQGR VPVRESPHHL AESFLFLPQV SPMDSGPWGC    240
ILTYRDGFN VSIMYNLTVL GLEPPTPLTV YAGAGSRVGL PCRLPAGVGT RSFLTAKWTP     300
PGGGPDLLVT GDNGDFTLRL EDVSQAQAGT YTCHIHLQEQ QLNATVTLAI ITVTPKSFGS    360
PGSLGKLLCE VTPVSGQERF VWSSLDTPSQ RSFSGPWLEA QEAQLLSQPW QCQLYQGERL    420
LGAAVYFTEL SSPGAQRSGR APGALPAGHL LLFLILGVLS LLLLVTGAFG FHLWRRQWRP    480
RRRFSALEQGI HPPQAQSKIE ELEQEPEPEP EPEPEPEPEP EPEQL                   525

SEQ ID NO: 24           moltype = DNA  length = 1575
FEATURE                 Location/Qualifiers
misc_feature            1..1575
                        note = full-length human LAG-3
source                  1..1575
                        mol_type = other DNA
                        organism = synthetic construct
SEQUENCE: 24
atgtgggagg ctcagttcct gggcttgctg tttctgcagc cgctttgggt ggctccagtg     60
aagcctctcc agccaggggc tgaggtcccg gtggtgtggg cccaggaggg ggctcctgcc    120
cagctcccct gcagcccac aatccccctc caggatctca gccttctgcg aagagcaggg     180
gtcacttggc agcatcagcc agacagtggc ccgcccgctg ccgccccgg ccatcccct      240
gcccccggcc ctcaccggc ggcgccctc tcctggggc caggccccg ccgctacacg        300
gtgctgagcg tgggtcccgg aggcctgcgc agcgggaggc tgcccctgca gcccgcgtc    360
cagctggatg agcgcggccg gcagcgcggg gacttctcgc tatggctgcg cccagccgg    420
cgcgcggacg cggcgagta ccgcgccgcg gtgcacctca gggaccgcgc cctctcctgc    480
cgcctccgtc tgcgctggg ccaggcctcg atgactgcca gcccccagat cctctcaga    540
gcctccgact gggtcatttt gaactgctcc ttcagccgcc ctgaccgccc agcctctgtg    600
cattggttcc ggaaccggg ccagggccga gtccctgtcc ggagtcccc catcaccac       660
ttagcggaaa gcttcctctt cctgcccaa gtcagcccca tggactctgg gcctggggc     720
tgcatcctca cctacagaga tggcttcaac gtctccatca tgtataacct cactgttctg    780
ggtctggagc cccccaactcc cttgacagtg tacgctggag caggttccag ggtggggctg   840
```

-continued

```
        ccctgccgcc tgcctgctgg tgtgggacc cggtctttcc tcactgccaa gtggactcct    900
        cctgggggag gccctgacct cctggtgact ggagacaatg gcgactttac ccttcgacta    960
        gaggatgtga gccaggccca ggctgggacc tacacctgcc atatccatct gcaggaacag   1020
        cagctcaatg ccactgtcac attggcaatc atcacagtga ctcccaaatc ctttgggtca   1080
        cctggatccc tggggaagct gctttgtgag gtgactccag tatctggaca agaacgcttt   1140
        gtgtggagct ctctggacac cccatcccaa aggagtttct caggaccttg gctggaggca   1200
        caggaggccc agtccctttc ccagccttgg caatgccagc tgtaccaggg ggagaggctt   1260
        cttggagcag cagtgtactt cacagagctg tctagcccag gtgcccaacg ctctgggaga   1320
        gccccaggtg ccctcccagc aggccacctc ctgctgtttc tcatccttgg tgtcctttct   1380
        ctgctcctt tggtgactgg agcctttggc tttcacctt ggagaagaca gtggcgacca    1440
        agacgatttt ctgccttaga gcaagggatt caccctccgc aggctcagag caagatagag   1500
        gagctggagc aagaaccgga gccggagccg gagccggaac cggagcccga gcccgagccc   1560
        gagccggagc agctc                                                    1575

SEQ ID NO: 25             moltype = AA   length = 521
FEATURE                   Location/Qualifiers
REGION                    1..521
                          note = full-length mouse LAG-3
source                    1..521
                          mol_type = protein
                          organism = synthetic construct
SEQUENCE: 25
MREDLLLGFL LLGLLWEAPV VSSGPGKELP VVWAQEGAPV HLPCSLKSPN LDPNFLRRGG   60
VIWQHQPDSG QPTPIPALDL HQGMPSPRQP APGRYTVLSV APGGLRSGRQ PLHPHVQLEE  120
RGLQRGDFSL WLRPALRTDA GEYHATVRLP NRALSCSLRL RVGQASMIAS PSGVLKLSDW  180
VLLNCSFSRP DRPVSVHWFQ GQNRVPVYNS PRHFLAETFL LLPQVSPLDS GTWGCVLTYR  240
DGFNVSITYN LKVLGLEPVA PLTVYAAEGS RVELPCHLPP GVGTPSLLIA KWTPPGGGPE  300
LPVAGKSGNF TLHLEAVGLA QAGTYTCSIH LQGQQLNATV TLAVITVTPK SFGLPGSRGK  360
LLCEVTPASG KERFVWRPLN NLSRSCPGPV LEIQEARLLA ERWQCQLYEG QRLLGATVYA  420
AESSSGAHSA RRISGDLKGG HLVLVLILGA LSLFLLVAGA FGFHWWRKQL LLRRFSALEH  480
GIQPFPAQRK IEELERELET EMGQEPEPEP EPQLEPEPRQ L                     521

SEQ ID NO: 26             moltype = DNA   length = 1563
FEATURE                   Location/Qualifiers
misc_feature              1..1563
                          note = full-length mouse LAG-3
source                    1..1563
                          mol_type = other DNA
                          organism = synthetic construct
SEQUENCE: 26
atgagggagg acctgctcct tggcttttg cttctgggac tgctttggga agctccagtt    60
gtgtcttcag ggcctgggaa agagctcccc gtggtgtggg cccaggaggg agctcccgtc   120
catcttccct gcagcctcaa atccccccaac ctggatccta acttctacg aagaggaggg   180
gttatctggc aacatcaacc agacagtggc caacccactc catcccggc ccttgacctt    240
caccagggga tgcccctcgcc tagacaaccc gcacccggtc gctacacggt gctgagcgtg   300
gctccaggag gcctgcgcag cgggaggcag ccctgcatc ccacgtgca gctggaggag    360
cgcggcctcc agcgcgggga cttctctctg tggttgccag cagctctgcg caccgatcgg   420
ggcgagtacc acgccaccgt gcgcctcccg aaccgcgccc tctcctgcag tctccgcctg   480
cgcgtcggcc aggcctcgat gattgctagt ccctcaggag tcctcaagct gtctgattgg   540
gtcctttga actgctcctt cagccgtcct gaccgcccag tctctgtgca ctggttccag   600
ggcagaaacc gagtgcctgt ctacaactca ccgcgtcatt ttttagctga aactttccgg   660
ttactgcccc aagtcagccc cctggactct gggacctggg gctgtgtcct cacctacaga   720
gatggcttca atgtctccat cacgtacaac ctcaaggttc tgggtctgga gcccgtagcc   780
cctctgacag tgtacgctgc tgaaggttct agggtgagc tgcccgtca tttgccccca    840
ggagtgggga ccccttcttt gctcattgcc aagtggactc ctcctggagg aggtcctgag   900
ctcccccgtgg ctggaaagag tggcaatttt acccttcacc ttgaggctgt gggtctggca   960
caggctggga cctacacctg tagcatccat ctgcagggac agcagctcaa tgccactgtc  1020
acgttggcgg tcatcacagt gactcccaaa tccttcgggt tacctggctc ccggggaag   1080
ctgttgtgtg aggtaacccc ggcatctgga aaggaaagat tggtgtggcg tcccctgaac  1140
aatctgtcca ggagttgccc gggcctgtg ctggagattc aggaggccag gctcctgct   1200
gagcgatggc agtgtcagct gtacgagggc cagaggcttc ttggagcgac agtgtacgcc  1260
gcagagtcta gctcaggcgc ccacagtgct aggagaatct caggtgacct aaaggaggc   1320
catctccgttc tcgttctcat ccttggtgcc ctctccctgt tccttttggt ggccggggcc  1380
tttggctttc actggtggag aaaacagttg ctactgagaa gatttctgc cttagaacat   1440
gggattcagc catttccggc tcagaggaag atagaggagc tggagcgaga actggagacg  1500
gagatgggac aggagccgga gccgagccg gagccacagc tggagccaga gcccaggcag  1560
ctc                                                                1563

SEQ ID NO: 27             moltype = AA   length = 533
FEATURE                   Location/Qualifiers
REGION                    1..533
                          note = full-length cynomolgus LAG-3
VARIANT                   74
                          note = X can be any naturally occurring amino acid
source                    1..533
                          mol_type = protein
                          organism = synthetic construct
SEQUENCE: 27
MWEAQFLGLL FLQPLWVAPV KPPQPGAEIS VVWAQEGAPA QLPCSPTIPL QDLSLLRRAG   60
```

```
VTWQHQPDSG PPAXAPGHPP VPGHRPAAPY SWGPRPRRYT VLSVGPGGLR SGRLPLQPRV    120
QLDERGRQRG DFSLWLRPAR RADAGEYRAT VHLRDRALSC RLRLRVGQAS MTASPPGSLR    180
TSDWVILNCS FSRPDRPASV HWFRSRGQGR VPVQGSPHHH LAESFLFLPH VGPMDSGLWG    240
CILTYRDGFN VSIMYNLTVL GLEPATPLTV YAGAGSRVEL PCRLPPAVGT QSFLTAKWAP    300
PGGGPDLLVA GDNGDFTLRL EDVSQAQAGT YICHIRLQGQ QLNATVTLAI ITVTPKSFGS    360
PGSLGKLLCE VTPASGQEHF VWSPLNTPSQ RSFSGPWLEA QEAQLLSQPW QCQLHQGERL    420
LGAAVYFTEL SSPGAQRSGR APGALRAGHL PLFLILGVLF LLLLVTGAFG FHLWRRQWRP    480
RRFSALEQGI HPPQAQSKIE ELEQEPELEP EPELERELGP EPEPGPEPEP EQL           533

SEQ ID NO: 28           moltype = DNA  length = 1599
FEATURE                 Location/Qualifiers
misc_feature            1..1599
                        note = full-length cynomolgus LAG-3
misc_difference         219..220
                        note = n is a, c, g, or t
source                  1..1599
                        mol_type = other DNA
                        organism = synthetic construct
SEQUENCE: 28
atgtgggagg ctcagttcct gggcttgctg tttctgcagc cgctctgggt ggctccagtg      60
aagcctcccc agccaggggc tgagatctcg gtggtgtggg cccaggaggg ggctcctgcc     120
cagctcccct gcagccccac aatccccctc caggatctca gccttctgca aagagcaggg     180
gtcacttggc agcatcaacc agacagtggc ccgcccgcnn ccgcccccgg ccacccccg      240
gtccccggcc atcgccggcc ggcgccctac tcttggggc ccaggcccg ccgctacacg       300
gtgctgagcg tgggtcctgg aggcctgcgc agcggggagc tgcccctgca gccccgcgtc     360
cagctggatg agcgcggccg gcagcgcggg gacttctcgc tgtggctgcg ccagcccgg     420
cgcgcggacg ccggcgagta ccgcgccacg gtgcacctca gggaccgcgc cctctcctgc     480
cgccttcgtc tgcgcgtggg ccaggcctcg atgactgcca gcccccaggt gtctctcagg     540
acctctgact gggtcatttt gaactgctcc ttcagccgcc ctgaccgcc agcctctgtg      600
cattggttcc ggagccgtgg ccagggccga gtccctgtcc aggggtcccc ccatcaccac     660
ttagcggaaa gcttcctctt cctgccccat gtcggcccca tggactctgg gctctggggc    720
tgcatcctca cctacagaga tggcttcaat gtctccatca tgtataacct cactgttctg    780
ggtctggagc ccgcaactcc cttgacagtg tacgctggag caggttccag ggtggagctg    840
ccctgccgcc tgcctcctgc tgtggggacc cagtcttttcc ttactgccaa gtgggctcct    900
cctgggggag gccctgacct cctggtggct ggagacaatg gcgactttac ccttcgacta    960
gaggatgtaa gccaggccca ggctgggacc tacatctgcc atatccgtct acagggacag   1020
cagctcaatg ccactgtcac attggcaatc atcacagtga ctcccaaatc ctttgggtca    1080
cctggctccc tggggaagct gctttgtgag gtgactccag catctggaca agaacacttt   1140
gtgtggagcc ccctgaacac cccatcccag aggagtttct caggaccatg gctggaggcc    1200
caggaagccc agctccttc ccagccttgg caatgccagc tgcaccaggg ggagaggctt     1260
cttggagcag cagtatactt cacagaactg tctagcccag gtgcacaacg ctctgggaga   1320
gccccagggg ccctccgagc aggccacctc ccgctgtttc tcatccttgg tgtcctttt    1380
ctgctccttt tggtgactgg agcctttggc tttcacctt ggagaagaca gtggcgacca    1440
agaagatttt ctgccttaga gcaagggatt caccctccgc aggctcagag caagatagag    1500
gagctcgagc aagaaccgga gctggaacca gagccggagc tggagcgcga gctggggccg    1560
gagcccgagc cggggcctga gcccgagccg gagcagctc                          1599
```

MONOCLONAL ANTIBODY AGAINST HUMAN LAG-3, METHOD FOR PREPARING THE SAME, AND USE THEREOF

RELATED APPLICATIONS

This application is a continuation of U.S. application Ser. No. 16/976,404, filed on Aug. 27, 2020, which is a U.S. National Phase application, filed under 35 U.S.C. § 371 (c), of International Application No. PCT/CN2019/076356, filed Feb. 27, 2019, which claims priority to, and the benefit of, International Application No. PCT/CN2018/077588, filed Feb. 28, 2018, and International Application No. PCT/CN2018/087504, filed May 18, 2018. Each of these documents is incorporated by reference herein in its entirety for all purposes.

INCORPORATION OF THE SEQUENCE LISTING

A Sequence Listing is provided herewith as a Sequence Listing XML, "CCPIT-027CON SEQ LIST", created on Sep. 21, 2023 and having a size of 46,637 bytes. The contents of the Sequence Listing XML are incorporated herein by reference in their entirety.

FIELD

This application generally relates to antibodies. More specifically, the application relates to fully human monoclonal antibodies that bind to human LAG-3, a method for preparing the same, and the use thereof.

BACKGROUND

Lymphocyte-activation gene 3 (CD223), also known as LAG-3, is a type I transmembrane protein that is a member of the immune-globulin superfamily (IgSF).

LAG-3 is a cell surface molecule expressed on activated T cells, NK cells, B cells and plasmacytoid dendritic cells, but not on resting T cells. LAG-3 shares approximately 20% amino acid sequence homology with CD4, but binds to MHC class II and a major LAG-3 functional ligand independent from MHC-II, i.e., fibrinogen-like protein 1 (FGL1) like molecule, with higher affinity, providing negative regulation of T cell receptor signaling.

Blockade of LAG-3 in vitro augments T cell proliferation and cytokine production, and LAG-3-deficient mice have a defect in the downregulation of T cell responses induced by the superantigen staphylococcal enterotoxin B, by peptides or by Sendai virus infection. LAG-3 is expressed on both activated natural Treg (nTreg) and induced CD4⁺FoxP3⁺ Treg (iTreg) cells, where expression levels are higher than that observed on activated effector CD4⁺ T cells. Blockade of LAG-3 on Treg cells abrogates Treg cell suppressor function whereas ectopic expression of LAG-3 in non-Treg CD4⁺ T cells confers suppressive activity. On the basis of the immunomodulatory role of LAG-3 on T cell function in chronic infection and cancer, the predicted mechanism of action for LAG-3-specific monoclonal antibodies is to inhibit the negative regulation of tumor-specific effector T cells.

There are only three potential antagonist antibodies that regulate LAG-3 function and anti-tumor immune responses in early clinical developments for the treatment of advanced solid tumors currently. These antibodies are described in patents US 20110150892 A1, US 20170101472 A1 and WO 2015138920 A1, and referred hereinafter as BMK1, BMK7 and BMK5 respectively. BMK8, as described herein, is humanized version of chimeric antibody BMK5. BMK1, BMK7 and BMK8 serve as benchmark antibodies in the context of the application. Accordingly, there remains a need for anti-human LAG-3 antibodies with improved efficacy, such as high binding affinity, low cross-family reactions and good stability. In this application, the inventors have generated a series of antibodies and fully human antibodies against LAG-3 utilizing humanized rats. The antibodies of the instant application have high binding affinity, specifically binding to human LAG-3 protein without cross-family reactions, and are potent to modulate immune responses.

SUMMARY

These and other objectives are provided for by the present disclosure which, in a broad sense, is directed to novel compounds, methods, compositions and articles of manufacture that provide antibodies with improved efficacy. The benefits provided by the present disclosure are broadly applicable in the field of antibody therapeutics and diagnostics and may be used in conjunction with antibodies that react with a variety of targets. The present disclosure provides antibodies, preferably fully human monoclonal antibodies that bind to human LAG-3. It also provides methods of hybridoma generation using humanized rats, nucleic acid molecules encoding the anti-LAG-3 antibodies, expression vectors and host cells used for the expression of anti-LAG-3 antibodies. The disclosure further provides the methods for validating the function of antibodies in vitro. The antibodies of the disclosure provide a potent agent for the treatment of multiple diseases via modulating human immune function.

In some aspects, the disclosure comprises an isolated antibody, or an antigen-binding portion thereof.

In some embodiments, the isolated antibody or the antigen-binding portion thereof has one or more of the following properties:
(a) binds to human LAG-3 with a $K_D$ of $2\times10^{-10}$ M or less;
(b) inhibits binding of LAG-3 to major histocompatibility (MHC) class II molecules;
(c) inhibits binding of LAG-3 to fibrinogen-like protein 1 (FGL1) ligand molecules;
(d) inhibits binding of LAG-3 to LSECtin and/or Galectin-3;
(e) binds to human LAG-3 without cross-family reactions; or
(f) has no cross-reactivity to human CD4.

In some embodiments, the isolated antibody or the antigen-binding portion thereof comprises:
A) one or more heavy chain CDRs (CDRHs) selected from at least one of the group consisting of: (i) a CDRH1 with at least 90% sequence identity to a CDRH1 as set forth in one of the sequences selected from the group consisting of SEQ ID NOs: 1 and 7; (ii) a CDRH2 with at least 90% sequence identity to a CDRH2 as set forth in one of the sequences selected from the group consisting of SEQ ID NOs: 2 and 8; and (iii) a CDRH3 with at least 90% sequence identity to a CDRH3 as set forth in one of the sequences selected from the group consisting of SEQ ID NOs: 3 and 9;
B) one or more light chain CDRs (CDRLs) selected from at least one of the group consisting of: (i) a CDRL1 with at least 90% sequence identity to a CDRL1 as set forth in one of the sequences selected from the group consisting of SEQ ID NOs: 4 and 10; (ii) a CDRL2 with at least 90% sequence identity to a CDRL2 as set forth in one of the sequences selected from the group consisting of SEQ ID NOs: 5 and 11; and (iii) a CDRL3 with at least 90% sequence identity to a CDRL3 as set forth in one of the sequences selected from the group consisting of SEQ ID NOs: 6 and 12; or C) one or more CDRHs of A) and one or more CDRLs of B).

In some embodiments, the isolated antibody or the antigen-binding portion thereof comprises:
A) one or more (such as 1, 2 or 3) heavy chain CDRs (CDRHs) selected from at least one of the group consisting of: (i) a CDRH1 selected from the group consisting of SEQ ID NOs: 1 and 7 or a CDRH1 that differs in amino acid sequence from the CDRH1 by an amino acid addition, deletion or substitution of not more than 2 amino acids; (ii) a CDRH2 selected from the group consisting of SEQ ID NOs: 2 and 8 or a CDRH2 that differs in amino acid sequence from the CDRH2 by an amino acid addition, deletion or substitution of not more than 2 amino acids; and (iii) a CDRH3 selected from the group consisting of SEQ ID NOs: 3 and 9 or a CDRH3 that differs in amino acid sequence from the CDRH3 by an amino acid addition, deletion or substitution of not more than 2 amino acids;
B) one or more (such as 1, 2 or 3) light chain CDRs (CDRLs) selected from at least one of the group consisting of: (i) a CDRL1 selected from the group consisting of SEQ ID NOs: 4 and 10 or a CDRL1 that differs in amino acid sequence from the CDRL1 by an amino acid addition, deletion or substitution of not more than 2 amino acids; (ii) a CDRL2 selected from the group consisting of SEQ ID NOs: 5 and 11 or a CDRL2 that differs in amino acid sequence from the CDRL2 by an amino acid addition, deletion or substitution of not more than 2 amino acids; (iii) a CDRL3 selected from the group consisting of SEQ ID NOs: 6 and 12 or a CDRL3 that differs in amino acid sequence from the CDRL3 by an amino acid addition, deletion or substitution of not more than 2 amino acids; or
C) one or more CDRHs of A) and one or more CDRLs of B).

In some embodiments, the isolated antibody or the antigen-binding portion thereof comprises:
A) a CDRH3 comprising SEQ ID NO: 3 or 9; or
B) a CDRH3 with at least 90% sequence identity to a CDRH3 as set forth in one of the sequences selected from the group consisting of SEQ ID NOs: 3 and 9; or
C) a CDRH3 that differs in amino acid sequence from the CDRH3 of A) by an amino acid addition, deletion or substitution of not more than 2 amino acids,
and wherein the isolated antibody or the antigen-binding portion thereof binds human LAG-3 with a $K_D$ of $2 \times 10^{-10}$ M or less.

In some embodiments, the isolated antibody or the antigen-binding portion thereof comprises:
(a) a CDRH1 comprising or consisting of SEQ ID NO: 1;
(b) a CDRH2 comprising or consisting of SEQ ID NO: 2;
(c) a CDRH3 comprising or consisting of SEQ ID NO: 3;
(d) a CDRL1 comprising or consisting of SEQ ID NO: 4;
(e) a CDRL2 comprising or consisting of SEQ ID NO: 5; and
(f) a CDRL3 comprising or consisting of SEQ ID NO: 6.

In some embodiments, the isolated antibody or the antigen-binding portion thereof comprises:
(a) a CDRH1 comprising or consisting of SEQ ID NO: 7;
(b) a CDRH2 comprising or consisting of SEQ ID NO: 8;
(c) a CDRH3 comprising or consisting of SEQ ID NO: 9;
(d) a CDRL1 comprising or consisting of SEQ ID NO: 10;
(e) a CDRL2 comprising or consisting of SEQ ID NO: 11; and
(f) a CDRL3 comprising or consisting of SEQ ID NO: 12.

In some embodiments, the isolated antibody or the antigen-binding portion thereof comprises:
(A) a heavy chain variable region:
(i) comprising the amino acid sequence of SEQ ID NO: 13;
(ii) comprising an amino acid sequence at least 85%, at least 90%, or at least 95% identical to SEQ ID NO: 13;
(iii) comprising an amino acid sequence with addition, deletion and/or substitution of one or more (such as 1-10, 1-5, 1-3, 1, 2, 3, 4, or 5) amino acids compared with SEQ ID NO: 13; and/or
(B) a light chain variable region:
(i) comprising the amino acid sequence of SEQ ID NO: 14;
(ii) comprising an amino acid sequence at least 85%, at least 90%, or at least 95% identical to SEQ ID NO: 14; or
(iii) comprising an amino acid sequence with addition, deletion and/or substitution of one or more (such as 1-10, 1-5, 1-3, 1, 2, 3, 4, or 5) amino acids compared with SEQ ID NO: 14.

In some embodiments, the isolated antibody or the antigen-binding portion thereof comprises:
(A) a heavy chain variable region:
(i) comprising the amino acid sequence of SEQ ID NO: 15;
(ii) comprising an amino acid sequence at least 85%, at least 90%, or at least 95% identical to SEQ ID NO: 15; or
(iii) comprising an amino acid sequence with addition, deletion and/or substitution of one or more (such as 1-10, 1-5, 1-3, 1, 2, 3, 4, or 5) amino acids compared with SEQ ID NO: 15; and/or
(B) a light chain variable region:
(i) comprising the amino acid sequence of SEQ ID NO: 16;
(ii) comprising an amino acid sequence at least 85%, at least 90%, or at least 95% identical to SEQ ID NO: 16; or
(iii) comprising an amino acid sequence with addition, deletion and/or substitution of one or more (such as 1-10, 1-5, 1-3, 1, 2, 3, 4, or 5) amino acids compared with SEQ ID NO: 16.

In some aspects, the disclosure is directed to an isolated nucleic acid molecule, comprising a nucleic acid sequence encoding the heavy chain variable region and/or the light chain variable region of the isolated antibody as disclosed herein.

In some aspects, the disclosure is directed to an expression vector comprising the nucleic acid molecule encoding the antibody or antigen-binding portion thereof as disclosed herein.

In some aspects, the disclosure is directed to a host cell comprising the expression vector as disclosed herein.

In some aspects, the disclosure is directed to a pharmaceutical composition comprising at least one antibody or antigen-binding portion thereof as disclosed herein and a pharmaceutically acceptable carrier.

In some aspects, the disclosure is directed to a method for preparing an anti-LAG-3 antibody or antigen-binding portion thereof which comprises expressing the antibody or antigen-binding portion thereof in the host cell and isolating the antibody or antigen-binding portion thereof from the host cell.

In some aspects, the disclosure is directed to a method of modulating an antigen-specific T cell response comprising administering to the subject the antibody or antigen-binding portion thereof as disclosed herein such that an antigen-specific T cell response is modulated in the subject.

In some aspects, the disclosure is directed to a method of modulating an immune response in a subject comprising administering the antibody or antigen-binding portion thereof as disclosed herein to the subject such that an immune response in the subject is modulated.

In some aspects, the disclosure is directed to a method for inhibiting or blocking the binding of LAG-3 to MHC class II molecules or FGL1 like molecules comprising contacting said MHC class II molecules or FGL1 like molecules with the antibody the antibody or antigen-binding portion thereof as disclosed herein.

In some aspects, the disclosure is directed to a method for inhibiting or blocking the binding of LAG-3 to LSECtin and/or Galectin-3 comprising contacting said LSECtin and/or Galectin-3 with the antibody the antibody or antigen-binding portion thereof as disclosed herein.

In some aspects, the disclosure is directed to a method for inhibiting growth of tumor cells in a subject comprising administering to the subject the antibody or antigen-binding portion thereof as disclosed herein such that growth of the tumor is inhibited in the subject.

In some aspects, the disclosure is directed to a method for treating viral infection in a subject comprising administering to the subject the antibody the antibody or antigen-binding portion thereof as disclosed herein such that the viral infection is treated in the subject.

In some aspects, the disclosure is directed to a method for treating or preventing proliferative disorders such as cancers in a subject comprising administering an effective amount of the antibody or antigen-binding portion thereof as disclosed herein to the subject.

In some aspects, the disclosure is directed to the use of the antibody or antigen-binding portion thereof as disclosed herein in the manufacture of a medicament for treating or preventing proliferative disorders such as cancers.

In some aspects, the disclosure is directed to the use of the antibody or antigen-binding portion thereof as disclosed herein in the manufacture of a diagnostic agent for diagnosing proliferative disorders such as cancers.

In some aspects, the disclosure is directed to the antibody or antigen-binding portion thereof as disclosed herein for use in treating or preventing proliferative disorders such as cancers.

In some aspects, the disclosure is directed to kits or devices and associated methods that employ the antibody or antigen-binding portion thereof as disclosed herein, and pharmaceutical compositions as disclosed herein, which are useful for the treatment of proliferative disorders such as cancer. To this end the present disclosure preferably provides an article of manufacture useful for treating such disorders comprising a receptacle containing the antibody or antigen-binding portion thereof as disclosed herein and instructional materials for using the antibody or antigen-binding portion thereof as disclosed herein to treat, ameliorate or prevent a proliferative disorder or progression or recurrence thereof. In selected embodiments, the devices and associated methods will comprise the step of contacting at least one circulating tumor cell with the antibody or antigen-binding portion thereof as disclosed herein.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Further, the contents of all references, patents and published patent applications cited throughout this application are incorporated herein in entirety by reference.

BRIEF DESCRIPTION OF THE FIGURES

FIG. 9A-B shows the result of epitope mapping.

DETAILED DESCRIPTION

Figure 1:
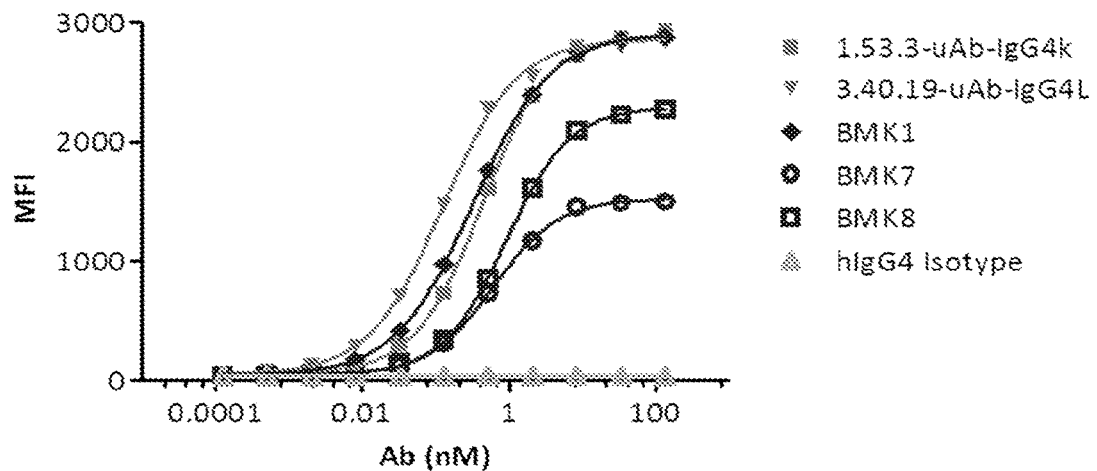
FIG. 1 shows the binding of LAG-3 antibodies to cell surface human LAG-3, expressed by MFI (Mean Fluorescence Intensity) and measured by BD FACSCanto II.

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised", is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. See, e.g., Abbas et al., Cellular and Molecular Immunology, $6^{th}$ ed., W. B. Saunders Company (2010); Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). The nomenclature used in connection with, and the laboratory procedures and techniques of, analytical chemistry, synthetic organic chemistry, and medicinal and pharmaceutical chemistry described herein are those well known and commonly used in the art. Moreover, any section headings used herein are for organizational purposes only and are not to be construed as limiting the subject matter described.

Definitions

In order to better understand the disclosure, the definitions and explanations of the relevant terms are provided as follows.

The term "antibody" or "Ab", as used herein, generally refers to a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a-heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "antigen-binding portion" or "antigen-binding fragment" of an antibody, which can be interchangeably used in the context of the application, refers to polypeptides comprising fragments of a full-length antibody, which retain the ability of specifically binding to an antigen that the full-length antibody specifically binds to, and/or compete with the full-length antibody for binding to the same antigen. Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')$_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides. Antigen binding fragments of an antibody may be obtained from a given antibody (e.g., the monoclonal anti-human LAG-3 antibody provided in the instant application) by conventional techniques known by a person skilled in the art (e.g., recombinant DNA technique or enzymatic or chemical cleavage methods), and may be screened for specificity in the same manner by which intact antibodies are screened.

The term "monoclonal antibody" or "mAb", as used herein, refer to a preparation of antibody molecules of single molecular composition. A monoclonal antibody displays a single binding specificity and affinity for a particular epitope.

The term "human antibody" or "fully human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody", as used herein, refers to antibodies displaying a single binding specificity, which have variable regions in which both the framework and CDR regions are derived from human germline immunoglobulin sequences.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody", as used herein, refer to antibodies in which the variable region sequences are derived from one species and the constant region sequences are derived from another species, such as an antibody in which the variable region sequences are derived from a mouse antibody and the constant region sequences are derived from a human antibody.

The term "LAG-3", as used herein, refers to Lymphocyte Activation Gene-3. The term "LAG-3" includes variants, isoforms, homologs, orthologs and paralogs.

The term "human LAG-3", as used herein, refers to human sequence LAG-3, such as the complete amino acid sequence of human LAG-3 having Genbank Accession No. NP_002277. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules or FGL1 like molecules.

The term "mouse LAG-3", as used herein, refers to mouse sequence LAG-3, such as the complete amino acid sequence of mouse LAG-3 having Genbank Accession No. NP 032505.

The term "cynomolgus LAG-3", as used herein, refers to cynomolgus sequence LAG-3, such as the complete amino acid sequence of cynomolgus LAG-3 having Genbank Accession No. XP_005570011.1.

The term "Ka", as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "high affinity" for an IgG antibody, as used herein, refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen.

The term "$EC_{50}$", as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The ability of "inhibit binding" or "compete for the same epitopes" in this application refers to the ability of an antibody or antigen-binding fragment thereof to inhibit the binding of two molecules (eg, human LAG-3 and human anti-LAG-3 antibody) to any detectable level. In certain embodiments, the binding of the two molecules can be inhibited at least 50% by the antibody or antigen-binding fragment thereof. In certain embodiments, such an inhibitory effect may be greater than 60%, greater than 70%, greater than 80%, or greater than 90%.

The term "epitope", as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731.

The term "isolated", as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other unpure substances that do not affect the activity of the isolated substance.

The term "isolated antibody", as used herein, is intended to refer to an antibody that is substantially free of other antibodies having different antigenic specificities (e.g., an isolated antibody that specifically binds a LAG-3 protein is substantially free of antibodies that specifically bind antigens other than LAG-3 proteins). An isolated antibody that specifically binds a human LAG-3 protein may, however, have cross-reactivity to other antigens, such as LAG-3 proteins from other species. Moreover, an isolated antibody can be substantially free of other cellular material and/or chemicals.

The term "vector", as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell", as used herein, refers to a cell into which a vector can be introduced, including, but not limited to, prokaryotic cell such as *E. coli* or *Bacillus subtilis*, fungal cell such as yeast cell or *Aspergillus*, insect cell such as S2 Drosophila cell or Sf9, and animal cell such as fibroblast, CHO cell, COS cell, NSO cell, HeLa cell, BHK cell, HEK 293 cell or human cell.

The term "identity", as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity", as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection", as used herein, refers to the process by which nucleic acids are introduced into eukaryotic cells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197. In a specific embodiment of the disclosure, human LAG-3 gene was transfected into 293F cells.

The term "hybridoma" and the term "hybridoma cell line", as used herein, may be used interchangeably. When the term "hybridoma" and the term "hybridoma cell line" are mentioned, they also include subclone and progeny cell of hybridoma.

The term "SPR" or "surface plasmon resonance", as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "fluorescence-activated cell sorting" or "FACS", as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017 Nov. 9). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "antibody-dependent cell-mediated cytotoxicity" or "ADCC", as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

The term "subject" includes any human or nonhuman animal, preferably humans.

The term "cancer", as used herein, refers to any or a tumor or a malignant cell growth, proliferation or metastasis-mediated, solid tumors and non-solid tumors such as leukemia and initiate a medical condition.

The term "treatment", "treating" or "treated", as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Specifically, the "therapeutically-effective amount," refers to an antibody or antigen-binding portion thereof in an amount or concentration effective to treat the human LAG-3-related diseases or conditions.

The present disclosure in a "host cell", as used herein, refers to a cell with the introduction of exogenous polynucleotides.

The term "pharmaceutically acceptable", as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

Anti-LAG-3 Antibodies

In some aspects, the disclosure comprises an isolated antibody or an antigen-binding portion thereof.

In the context of the application, the "antibody" may include polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; and derivatives thereof including Fc fusions and other modifications, and any other immunoreactive molecule so long as it exhibits preferential association or binding with a LAG-3 protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). In a preferred embodiment, the antibody is a monoclonal antibody. In a more preferred embodiment, the antibody is a human monoclonal antibody.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., Barbas et al., *Proc. Natl. Acad. Sci. USA* 88:7978-7982 (1991)).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and 6,075,181 and 6,150,584 regarding XenoMouse® technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., J. Immunol, 147 (1):86-95 (1991); and U.S. Pat. No. 5,750,373.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, 1$^{st}$ ed. 2009; Shire et. al. (eds.) *Current Trends in Monoclonal Antibody Development and Manufacturing*, Springer Science+Business Media LLC, 1$^{st}$ ed. 2010; Harlow et al., Antibodies: A Laboratory Manual, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this disclosure. In a preferred embodiment, the anti-human LAG-3 monoclonal antibody is prepared by using hybridoma.

Generation of Hybridomas Producing Human Monoclonal Antibodies of the Disclosure To generate hybridomas producing the antibodies of the disclosure, for instance, human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) Antibodies, A Laboratory Manual, Cold Spring Harbor Publications, New York.

Generation of Transfectomas Producing Monoclonal Antibodies of the Disclosure

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, CA (1990)). Exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe et al. (1988) MoI. Cell. Biol. 8:466-472). The expression vector and expression control sequences are chosen to be compatible with the expression host cell used.

The antibody light chain gene and the antibody heavy chain gene can be inserted into the same or separate expression vectors. In some embodiments, the variable regions are used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express the antibodies of the disclosure in either prokaryotic or eukaryotic host cells, for example, mammalian host cells, which can assemble and secrete a properly folded and immunologically active antibody.

Mammalian host cells for expressing the recombinant antibodies of the disclosure include Chinese Hamster Ovary (CHO cells) (including dhfr" CHO cells, described in Urlaub and Chasin, (1980) Proc. Natl. Acad. ScL USA 77:4216-4220, used with a DHFR selectable marker, e.g., as described in R. J. Kaufman and P. A. Sharp (1982) J. MoI. Biol. 159:601-621), NSO myeloma cells, COS cells and SP2 cells. In particular, for use with NSO myeloma cells, another expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

Anti-LAG-3 Antibodies With Certain Properties

The antibodies of the disclosure are characterized by particular functional features or properties of the antibodies. In some embodiments, the isolated antibody or the antigen-binding portion thereof has one or more of the following properties:

(a) binds to human LAG-3 with a $K_D$ of $2 \times 10^{-10}$ M or less;
(b) inhibits binding of LAG-3 to major histocompatibility (MHC) class II molecules;
(c) inhibits binding of LAG-3 to fibrinogen-like protein 1 (FGL1) ligand molecules;

(d) inhibits binding of LAG-3 to LSECtin and/or Galectin-3; or
(e) binds to human LAG-3 without cross-family reactions.

The antibody of the disclosure binds to human LAG-3 with high affinity. The binding of an antibody of the disclosure to LAG-3 can be assessed using one or more techniques well established in the art, for instance, ELISA. The binding specificity of an antibody of the disclosure can also be determined by monitoring binding of the antibody to cells expressing a LAG-3 protein, e.g., flow cytometry. For example, an antibody can be tested by a flow cytometry assay in which the antibody is reacted with a cell line that expresses human LAG-3, such as CHO cells that have been transfected to express LAG-3 on their cell surface. Other suitable cells for use in flow cytometry assays include anti-CD3-stimulated CD4+ activated T cells, which express native LAG-3. Additionally or alternatively, the binding of the antibody, including the binding kinetics (e.g., Kd value) can be tested in BIAcore binding assays. Still other suitable binding assays include ELISA assays, for example using a recombinant LAG-3 protein. For instance, an antibody of the disclosure binds to a human LAG-3 protein with a $K_D$ of $5 \times 10^{-8}$ M or less, binds to a human LAG-3 protein with a $K_D$ of $2 \times 10^{-8}$ M or less, binds to a human LAG-3 protein with a $K_D$ of $5 \times 10^{-9}$ M or less, binds to a human LAG-3 protein with a $K_D$ of $4 \times 10^{-9}$ M or less, binds to a human LAG-3 protein with a $K_D$ of $3 \times 10^{-9}$ M or less, binds to a human LAG-3 protein with a $K_D$ of $2 \times 10^{-9}$ M or less, binds to a human LAG-3 protein with a $K_D$ of $1 \times 10^{-9}$ M or less, binds to a human LAG-3 protein with a $K_D$ of $5 \times 10^{-10}$ M or less, or binds to a human LAG-3 protein with a $K_D$ of $1 \times 10^{-10}$ M or less.

The ability of the antibody to modulate an immune response, such as an antigen-specific T cell response, can be indicated by, for example, the ability of the antibody to stimulate interleukin-2 (IL-2) production in an antigen-specific T cell response. In certain embodiments, an antibody of the disclosure binds to human LAG-3 and exhibits an ability to stimulate an antigen-specific T cell response. Means by which to evaluate the ability of the antibody to stimulate an immune response may include the ability of the antibody to inhibit tumor growth, such as in an in vivo tumor graft model or the ability of the antibody to stimulate an autoimmune response.

The isolated antibody or the antigen-binding portion thereof as disclosed herein inhibits binding of LAG-3 to major histocompatibility (MHC) class II molecules, FGL1 like molecules, LSECtin and/or Galectin-3. LAG-3 negatively regulates T cell signaling and functions. Ligands for LAG-3 includes, e.g., major histocompatibility (MHC) Class II molecules, LSECtin and Galectin-3. LAG-3 can interact with MHC class II molecules on the cell surface (Baixeras et al. (1992) J.

Exp. Med. 176:327-337; Huard et al. (1996) Eur. J. Immunol. 26: 1180-1186). It has been suggested that the direct binding of LAG-3 to MHC class II plays a role in down-regulating antigen-dependent stimulation of CD4+ T lymphocytes (Huard et al. (1994) Eur. J. Immunol. 24:3216-3221). Recently, Chen Lieping et al. have further demonstrated, through in vitro experiments, that FGL1 is a major immune inhibitory ligand of LAG-3, and thus, they have proposed a novel tumor immune evasion pathway FGL1-LAG-3, and blocking the FGL1-LAG-3 interaction may increase anti-tumor effect (Cell. 2019 Jan. 10; 176(1-2):334-347.e12).

Galectin-3 is a 31 kD lectin that modulates T cell responses through several mechanisms including apoptosis, TCR cross linking, and TCR down regulation. Galectin-3 binds to LAG-3, and LAG-3 expression is necessary for galectin-3 mediated suppression of CD8+ T cells in vitro. (Kouo et al. (2015) Cancer Immunol. Res. 10.1158: 2326-6066). Anti-LSECtin has been shown to inhibit B16 melanoma cell growth (Xu et al. (2014) Cancer Res. 74(13): 3418-3428).

Anti-LAG-3 Antibodies Comprising CDRs With Sequence Identity to Specific Sequences In some embodiments, the isolated antibody or the antigen-binding portion thereof comprises:
A) one or more heavy chain CDRs (CDRHs) selected from at least one of the group consisting of: (i) a CDRH1 with at least 90% sequence identity to a CDRH1 as set forth in one of the sequences selected from the group consisting of SEQ ID NOs: 1 and 7; (ii) a CDRH2 with at least 90% sequence identity to a CDRH2 as set forth in one of the sequences selected from the group consisting of SEQ ID NOs: 2 and 8; and (iii) a CDRH3 with at least 90% sequence identity to a CDRH3 as set forth in one of the sequences selected from the group consisting of SEQ ID NOs: 3 and 9;
B) one or more light chain CDRs (CDRLs) selected from at least one of the group consisting of: (i) a CDRL1 with at least 90% sequence identity to a CDRL1 as set forth in one of the sequences selected from the group consisting of SEQ ID NOs: 4 and 10; (ii) a CDRL2 with at least 90% sequence identity to a CDRL2 as set forth in one of the sequences selected from the group consisting of SEQ ID NOs: 5 and 11; and (iii) a CDRL3 with at least 90% sequence identity to a CDRL3 as set forth in one of the sequences selected from the group consisting of SEQ ID NOs: 6 and 12; or
C) one or more CDRHs of A) and one or more CDRLs of B).

The assignment of amino acids to each CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al.,1996, PMID: 8876650; or Dubel, Ed. (2007) *Handbook of Therapeutic Antibodies*, 3$^{rd}$ Ed., Wily-VCH Verlag GmbH and Co. unless otherwise noted.

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, NY, 2001 and Dinarello et al., Current Protocols in Immunology, John Wiley and Sons Inc., Hoboken, NJ, 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.:

Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs {e.g., XBLAST and NBLAST) can be used. See www.ncbi.nlm.nih.gov.

In other embodiments, the CDR amino acid sequences can be at least 90%, 91%, 92%, 93%, 94%, 95%, 96%, 97%, 98% or 99% identical to the respective sequences set forth above. As an illustrative example, the antibody may comprise a CDRH1 with at least 90%, 91%, 92%, 93%, 94%, 95%, 96%, 97%, 98% or 99% sequence identity to a CDRH1 as set forth in one of the sequences selected from the group consisting of SEQ ID NOs: 1 and 7.

Anti-LAG-3 Antibodies Comprising CDRs With Amino Acid Addition, Deletion or Substitution In some embodiments, the isolated antibody or the antigen-binding portion thereof comprises:
A) one or more heavy chain CDRs (CDRHs) selected from at least one of the group consisting of: (i) a CDRH1 selected from the group consisting of SEQ ID NOs: 1 and 7 or a CDRH1 that differs in amino acid sequence from the CDRH1 by an amino acid addition, deletion or substitution of not more than 2 amino acids; (ii) a CDRH2 selected from the group consisting of SEQ ID NOs: 2 and 8 or a CDRH2 that differs in amino acid sequence from the CDRH2 by an amino acid addition, deletion or substitution of not more than 2 amino acids; and (iii) a CDRH3 selected from the group consisting of SEQ ID NOs: 3 and 9 or a CDRH3 that differs in amino acid sequence from the CDRH3 by an amino acid addition, deletion or substitution of not more than 2 amino acids;
B) one or more light chain CDRs (CDRLs) selected from at least one of the group consisting of: (i) a CDRL1 selected from the group consisting of SEQ ID NOs: 4 and 10 or a CDRL1 that differs in amino acid sequence from the CDRL1 by an amino acid addition, deletion or substitution of not more than 2 amino acids; (ii) a CDRL2 selected from the group consisting of SEQ ID NOs: 5 and 11 or a CDRL2 that differs in amino acid sequence from the CDRL2 by an amino acid addition, deletion or substitution of not more than 2 amino acids; and (iii) a CDRL3 selected from the group consisting of SEQ ID NOs: 6 and 12 or a CDRL3 that differs in amino acid sequence from the CDRL3 by an amino acid addition, deletion or substitution of not more than 2 amino acids; or
C) one or more CDRHs of A) and one or more CDRLs of B).

Preferably, the CDRs of the isolated antibody or the antigen-binding portion thereof contain a conservative substitution of not more than 2 amino acids, or not more than 1 amino acid. The term "conservative substitution", as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Anti-LAG-3 Antibodies Comprising CDRs

In some embodiments, the isolated antibody or the antigen-binding portion thereof comprises:
(a) a CDRH1 comprising SEQ ID NO: 1;
(b) a CDRH2 comprising SEQ ID NO: 2;
(c) a CDRH3 comprising SEQ ID NO: 3;
(d) a CDRL1 comprising SEQ ID NO: 4;
(e) a CDRL2 comprising SEQ ID NO: 5; and
(f) a CDRL3 comprising SEQ ID NO: 6.

In a specific embodiment, the isolated antibody or the antigen-binding portion thereof comprises:
(a) a CDRH1 consisting of SEQ ID NO: 1;
(b) a CDRH2 consisting of SEQ ID NO: 2;
(c) a CDRH3 consisting of SEQ ID NO: 3;
(d) a CDRL1 consisting of SEQ ID NO: 4;
(e) a CDRL2 consisting of SEQ ID NO: 5; and
(f) a CDRL3 consisting of SEQ ID NO: 6.

In some embodiments, the isolated antibody or the antigen-binding portion thereof comprises:
(a) a CDRH1 comprising SEQ ID NO: 7;
(b) a CDRH2 comprising SEQ ID NO: 8;
(c) a CDRH3 comprising SEQ ID NO: 9;
(d) a CDRL1 comprising SEQ ID NO: 10;
(e) a CDRL2 comprising SEQ ID NO: 11; and
(f) a CDRL3 comprising SEQ ID NO: 12.

In a specific embodiment, the isolated antibody or the antigen-binding portion thereof comprises:
(a) a CDRH1 consisting of SEQ ID NO: 7;
(b) a CDRH2 consisting of SEQ ID NO: 8;
(c) a CDRH3 consisting of SEQ ID NO: 9;
(d) a CDRL1 consisting of SEQ ID NO: 10;
(e) a CDRL2 consisting of SEQ ID NO: 11; and
(f) a CDRL3 consisting of SEQ ID NO: 12.

Anti-LAG-3 Antibodies Comprising a Heavy Chain Variable Region and a Light Chain Variable Region In some embodiments, the isolated antibody or the antigen-binding portion thereof comprises:
(A) a heavy chain variable region:
(i) comprising the amino acid sequence of SEQ ID NO: 13;
(ii) comprising an amino acid sequence at least 85%, at least 90%, or at least 95% identical to SEQ ID NO: 13; or
(iii) comprising an amino acid sequence with addition, deletion and/or substitution of one or more amino acids compared with SEQ ID NO: 13; and/or
(B) a light chain variable region:
(i) comprising the amino acid sequence of SEQ ID NO: 14;
(ii) comprising an amino acid sequence at least 85%, at least 90%, or at least 95% identical to SEQ ID NO: 14;
(iii) comprising an amino acid sequence with addition, deletion and/or substitution of one or more amino acids compared with SEQ ID NO: 14.

In a specific embodiment, the isolated antibody or the antigen-binding portion thereof comprises:
(a) a heavy chain variable region consisting of the amino acid sequence of SEQ ID NO: 13; and/or
(b) a light chain variable region comprising the amino acid sequence of SEQ ID NO: 14.

In some embodiments, the isolated antibody or the antigen-binding portion thereof comprises:
(A) a heavy chain variable region:
(i) comprising the amino acid sequence of SEQ ID NO: 15;
(ii) comprising an amino acid sequence at least 85%, at least 90%, or at least 95% identical to SEQ ID NO: 15; or
(iii) comprising an amino acid sequence with addition, deletion and/or substitution of one or more amino acids compared with SEQ ID NO: 15; and/or
(B) a light chain variable region:
(i) comprising the amino acid sequence of SEQ ID NO: 16;
(ii) comprising an amino acid sequence at least 85%, at least 90%, or at least 95% identical to SEQ ID NO: 16; or
(iii) comprising an amino acid sequence with addition, deletion and/or substitution of one or more amino acids compared with SEQ ID NO: 16.

In a specific embodiment, the isolated antibody or the antigen-binding portion thereof comprises:
(a) a heavy chain variable region consisting of the amino acid sequence of SEQ ID NO: 15; and/or
(b) a light chain variable region comprising the amino acid sequence of SEQ ID NO: 16.

In other embodiments, the amino acid sequences of the heavy chain variable region and/or the light chain variable region can be at least 85%, 86%, 87%, 88%, 89%, 90%, 91%, 92%, 93%, 94%, 95%, 96%, 97%, 98% or 99% identical to the respective sequences set forth above. As an illustrative example, the antibody may comprise a heavy chain variable region with at least 85%, 86%, 87%, 88%, 89%, 90%, 91%, 92%, 93%, 94%, 95%, 96%, 97%, 98% or 99% sequence identity to a heavy chain variable region consisting of the amino acid sequence of SEQ ID NO: 15.

In some further embodiments, the isolated antibody or the antigen-binding portion thereof may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43.

As described above, the term "conservative substitution", as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Binning and Epitope Mapping

It will further be appreciated the disclosed antibodies will associate with, or bind to, discrete epitopes or immunogenic determinants presented by the selected target or fragment thereof. In certain embodiments, epitope or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In certain embodiments, an antibody is said to specifically bind (or immunospecifically bind or react) an antigen when it preferentially recognizes its target antigen in a complex mixture of proteins and/or macromolecules. In some embodiments, an antibody is said to specifically bind an antigen when the equilibrium dissociation constant ($K_D$) is less than or equal to $10^{-6}$M or less than or equal to $10^{-7}$M, more preferably when the e $K_D$ is less than or equal to $10^{-8}$M, and even more preferably when the $K_D$ is less than or equal to $10^{-9}$M.

Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect, it will be appreciated that, in certain embodiments, an epitope may be associated with, or reside in, one or more regions, domains or motifs of, for example, the LAG-3 protein. Similarly, the art-recognized term "motif" will be used in accordance with its common meaning and shall generally refer to a short, conserved region of a protein that is typically ten to twenty contiguous amino acid residues.

In any event once a desired epitope on an antigen is determined, it is possible to generate antibodies to that epitope, e.g., by immunizing with a peptide comprising the epitope using techniques described in the present disclosure. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

As used herein, the term "binning" refers to methods used to group or classify antibodies based on their antigen binding characteristics and competition. While the techniques are useful for defining and categorizing the antibodies of the instant disclosure, the bins do not always directly correlate with epitopes and such initial determinations of epitope binding may be further refined and confirmed by other art-recognized methodology in the art and as described herein. However, it will be appreciated that empirical assignment of the antibodies to individual bins provides information that may be indicative of the therapeutic potential of the disclosed antibodies.

More specifically, one can determine whether a selected reference antibody (or fragment thereof) binds to the same epitope or cross competes for binding with a second test antibody (i.e., is in the same bin) by using methods known in the art and set forth in the Examples herein.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

Nucleic Acid Molecules Encoding Antibodies of the Disclosure

In some aspects, the disclosure is directed to an isolated nucleic acid molecule, comprising a nucleic acid sequence encoding the heavy chain variable region and/or the light chain variable region of the isolated antibody as disclosed herein.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

The isolated nucleic acid encoding the VH region can be converted to a full-length heavy chain gene by operatively linking the VH-encoding nucleic acid to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but more preferably is an IgG1 or IgG4 constant region, and most preferably is an IgG4 constant region.

The isolated nucleic acid encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

Preferred nucleic acids molecules of the disclosure are those encoding the VH and VL sequences of 1.53.3-uAb-IgG4k and 3.40.19-uAb-IgG4L monoclonal antibodies. DNA sequences encoding the VH sequences of 1.53.3-uAb-IgG4k and 3.40.19-uAb-IgG4L are shown in SEQ ID NOs: 17 and 19, respectively. DNA sequences encoding the VL sequences of 1.53.3-uAb-IgG4k and 3.40.19-uAb-IgG4L are shown in SEQ ID NOs: 18 and 20, respectively. In some embodiments, the nucleic acids share an at least 80% (e.g. at least 85%, 86%, 87%, 88%, 89%, 90%, 91%, 92%, 93%, 94%, 95%, 96%, 97%, 98%, or 99%) sequence identity to SEQ ID NOs: 17-20, respectively. In some embodiments, the percentage of identity is derived from the degeneracy of the genetic code, and the encoded protein sequences remain unchanged.

Pharmaceutical Compositions

In some aspects, the disclosure is directed to a pharmaceutical composition comprising at least one antibody or antigen-binding portion thereof as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, an antiviral agent, or a vaccine, such that the anti-LAG-3 antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present disclosure, in a solvent containing an antibody or an antigen-binding fragment of the present disclosure discloses compositions include one or more anti-oxidants such as methionine, reducing antibody or antigen binding fragment thereof may be oxidized. The oxidation reduction may prevent or reduce a decrease in binding affinity, thereby enhancing antibody stability and extended shelf life. Thus, in some embodiments, the present disclosure provides a composition comprising one or more antibodies or antigen binding fragment thereof and one or more anti-oxidants such as methionine. The present disclosure further provides a variety of methods, wherein an antibody or antigen binding fragment thereof is mixed with one or more anti-oxidants, such as methionine, so that the antibody or antigen binding fragment thereof can be prevented from oxidation, to extend their shelf life and/or increased activity.

Administration, Formulation and Dosage

The pharmaceutical composition of the disclosure may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, i.e., dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the antibody or the antigen binding portion thereof of the disclosure may be administered in various ranges. These include about 5 μg/kg body weight to about 100 mg/kg body weight per dose; about 50 μg/kg body weight to about 5 mg/kg body weight per dose; about 100 μg/kg body weight to about 10 mg/kg body weight per dose. Other ranges include about 100 μg/kg body weight to about 20 mg/kg body weight per dose and about 0.5 mg/kg body weight to about 20 mg/kg body weight per dose. In certain embodiments, the dosage is at least about 100 μg/kg body weight, at least about 250 μg/kg body weight, at least about 750 μg/kg body weight, at least about 3 mg/kg body weight, at least about 5 mg/kg body weight, at least about 10 mg/kg body weight.

In any event, the antibody or the antigen binding portion thereof of the disclosure is preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody or the antigen-binding portion thereof of the instant disclosure will comprise multiple doses of the selected drug product over a period of weeks or months. More specifically, the antibody or the antigen-binding portion thereof of the instant disclosure may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) will comprise the antibody or antigen-binding portion thereof in concentrations of from about 10 μg/mL to about 100 mg/mL. In certain selected embodiments, the concentrations of the antibody or the antigen binding portion thereof will comprise 20 μg/mL, 40 μg/mL, 60 μg/mL, 80 μg/mL, 100 μg/mL, 200 μg/mL, 300, μg/mL, 400 μg/mL, 500 μg/mL, 600 μg/mL, 700 μg/mL, 800 μg/mL, 900 μg/mL or 1 mg/mL. In other preferred embodiments ADC concentrations will comprise 2 mg/mL, 3 mg/mL, 4 mg/mL, 5 mg/mL, 6 mg/mL, 8 mg/mL, 10 mg/mL, 12 mg/mL, 14 mg/mL, 16 mg/mL, 18 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL or 100 mg/mL.

Applications

The antibodies, antibody compositions and methods of the present disclosure have numerous in vitro and in vivo utilities involving, for example, detection of LAG-3 or enhancement of immune response by blockade of LAG-3. For example, these molecules can be administered to cells in culture, in vitro or ex vivo, or to human subjects, e.g., in vivo, to enhance immunity in a variety of situations. The immune response can be modulated, for instance, augmented, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-LAG-3 antibodies can be administered together with an antigen of interest or the antigen may already be present in the subject to be treated (e.g., a tumor-bearing or virus-bearing subject). When antibodies to LAG-3 are administered together with another agent, the two can be administered in either order or simultaneously.

The disclosure further provides methods for detecting the presence of human LAG-3 antigen in a sample, or measuring the amount of human LAG-3 antigen, comprising contacting the sample, and a control sample, with a human monoclonal antibody, or an antigen binding portion thereof, which specifically binds to human LAG-3, under conditions that allow for formation of a complex between the antibody or portion thereof and human LAG-3. The formation of a complex is then detected, wherein a difference complex formation between the sample compared to the control sample is indicative of the presence of human LAG-3 antigen in the sample. Moreover, the anti-LAG-3 antibodies of the disclosure can be used to purify human LAG-3 via immunoaffinity purification.

Given the ability of anti-LAG-3 antibodies of the disclosure to inhibit the binding of LAG-3 to MHC Class II molecules or FGL1 like molecules and to stimulate antigen-specific T cell responses, the disclosure also provides in vitro and in vivo methods of using the antibodies of the disclosure to stimulate, enhance or upregulate antigen-specific T cell responses. For example, the disclosure provides a method of stimulating an antigen-specific T cell response comprising administering to the subject the antibody of the disclosure or an antigen binding portion thereof such that an antigen-specific T cell response is stimulated. Any suitable indicator of an antigen-specific T cell response can be used to measure the antigen-specific T cell response.

Treatment of Cancers

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated. The disclosure also provides a method of stimulating an immune response (e.g., an antigen-specific T cell response) in a subject comprising administering an antibody or an antigen binding portion thereof of the disclosure to the subject such that an immune response (e.g., an antigen-specific T cell response) in the subject is stimulated. In a preferred embodiment, the subject is a cancer-bearing subject and an immune response against the tumor is stimulated. Cancer Blockade of LAG-3 by antibodies can enhance the immune response to cancerous cells in the patient. An anti-LAG-3 antibody can be used alone to or used in conjunction with other immunogenic agents, standard cancer treatments, or other antibodies.

Examples of cancers that can be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

The antibody or the antigen-binding portion thereof may be used in combination with chemical therapies or radiotherapies.

Combined Use With Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, in certain embodiments selected anti-cancer agents will be linked to the unpaired cysteines of the engineered antibodies to provide engineered conjugates as set forth herein. Accordingly, such engineered conjugates are expressly contemplated as being within the scope of the instant disclosure. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In certain embodiments, the substance is a naturally occurring molecule derived from a living organism. Examples of cytotoxic agents include, but are not limited to, small molecule toxins or enzymatically active toxins of bacteria (e.g., Diptheria toxin, Pseudomonas endotoxin and exotoxin, Staphylococcal enterotoxin A), fungal (e.g., a-sarcin, restrictocin), plants (e.g., abrin, ricin, modeccin, viscumin, pokeweed anti-viral protein, saporin, gelonin, momoridin, trichosanthin, barley toxin, Aleurites fordii proteins, dianthin proteins, Phytolacca mericana proteins (PAPI, PAPII, and PAP-S), Momordica charantia inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant disclosure a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present disclosure (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib,sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Combined Use With Radiotherapies

The present disclosure also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

Diagnosis

The disclosure provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments, the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

Pharmaceutical Packs and Kits

Pharmaceutical packs and kits comprising one or more containers, comprising one or more doses of the antibody or the antigen-binding portion thereof are also provided. In certain embodiments, a unit dosage is provided wherein the unit dosage contains a predetermined amount of a composition comprising, for example, the antibody or the antigen-binding portion thereof, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the conjugate composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container (s) indicates that the enclosed conjugate composition is used for treating the neoplastic disease condition of choice.

The present disclosure also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody or the antigen-binding portion thereof of the disclosure such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody or the antigen-binding portion thereof, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other component in close confinement for commercial sale, such as, e.g., injection or blow-molded plastic containers into which the desired vials and other apparatus are placed and retained.

Sequence Listing Summary

Appended to the instant application is a sequence listing comprising a number of nucleic acid and amino acid sequences. The following table provides a summary of the included sequences.

| SEQ ID NO. | Description |
|---|---|
| 1 | CDRH1 of 1.53.3-uAb-IgG4k |
| 2 | CDRH2 of 1.53.3-uAb-IgG4k |
| 3 | CDRH3 of 1.53.3-uAb-IgG4k |
| 4 | CDRL1 of 1.53.3-uAb-IgG4k |
| 5 | CDRL2 of 1.53.3-uAb-IgG4k |
| 6 | CDRL3 of 1.53.3-uAb-IgG4k |
| 7 | CDRH1 of 3.40.19-uAb-IgG4L |
| 8 | CDRH2 of 3.40.19-uAb-IgG4L |
| 9 | CDRH3 of 3.40.19-uAb-IgG4L |
| 10 | CDRL1 of 3.40.19-uAb-IgG4L |
| 11 | CDRL2 of 3.40.19-uAb-IgG4L |
| 12 | CDRL3 of 3.40.19-uAb-IgG4L |
| 13 | VH of 1.53.3-uAb-IgG4k |
| 14 | VL of 1.53.3-uAb-IgG4k |
| 15 | VH of 3.40.19-uAb-IgG4L |
| 16 | VL of 3.40.19-uAb-IgG4L |
| 17 | DNA sequence encoding VH of 1.53.3-uAb-IgG4k |
| 18 | DNA sequence encoding VL of 1.53.3-uAb-IgG4k |
| 19 | DNA sequence encoding VH of 3.40.19-uAb-IgG4L |
| 20 | DNA sequence encoding VL of 3.40.19-uAb-IgG4L |
| 21 | Amino acid sequence of human LAG-3 ECD |
| 22 | DNA sequence encoding human LAG-3 ECD |
| 23 | Amino acid sequence of full-length human LAG-3 |
| 24 | DNA sequence encoding full-length human LAG-3 |
| 25 | Amino acid sequence of full-length mouse LAG-3 |
| 26 | DNA sequence encoding full-length mouse LAG-3 |
| 27 | Amino acid sequence of full-length cynomolgus LAG-3 |
| 28 | DNA sequence encoding full-length cynomolgus LAG-3 |

EXAMPLES

The present disclosure, thus generally described, will be understood more readily by reference to the following Examples, which are provided by way of illustration and are not intended to be limiting of the instant disclosure. The Examples are not intended to represent that the experiments below are all or the only experiments performed.

Example 1

Preparation of Materials

1. Immunogen Generation

Nucleic acid encoding human LAG-3 ECD (extracellular domain, ECD) with SEQ ID NO: 22 or full-length human LAG-3 with SEQ ID NO: 24 was synthesized by Sangon Biotech. The amino acid sequence of LAG-3 ECD and the DNA sequence encoding the same are shown in SEQ ID NOs: 21 and 22, and the amino acid sequence of full-length LAG-3 and the DNA sequence encoding the same are shown in SEQ ID NOs: 23 and 24, respectively. LAG-3 gene fragments were amplified from the synthesized nucleic acid and inserted into the expression vector pcDNA3.3 (ThermoFisher). The inserted LAG-3 gene fragment was further confirmed by DNA sequencing. Fusion proteins containing human LAG-3 ECD with various tags, including human Fc, mouse Fc and His tags, were obtained by transfection of human LAG-3 gene into 293F cells (ThermoFisher). The cells were cultured in a FreeStyle 293 Expression Medium (ThermoFisher) at 37° C., 5% $CO_2$. After 5 days of culture, supernatants harvested from the culture of transiently transfected cells were used for protein purification. The fusion proteins were purified by nickel, protein A and/or SEC column. An untagged LAG-3 ECD protein was generated by cleavage of ECD-hFc fusion protein with a cut site using Factor Xa protease (New England Biolabs). Purified proteins were used for immunization, screening and characterization.

2. Production of Benchmark Antibodies

Gene sequences of anti-human LAG-3 benchmark antibodies (BMK1 and BMK7) were synthesized based on the information disclosed in patent applications US20110150892 A1 and US 20170101472 A1 (BMK1 was referred to as "25F7" in US20110150892 A1) and (BMK7 was referred to as "H4sH15482P" in US 20170101472 A1), respectively. Benchmark antibody BMK8 is the humanized version of chimeric antibody BMKS which was described in WO2015138920 A1 and referred to as "BAP050-chi". BMK8 was referred to as "BAP050-hum01" in WO2015138920 A1. The synthesized gene sequences were incorporated into plasmids pcDNA3.3, as described in above section 1. The plasmids were transiently transfected into 293F cells. The cells were cultured in the same way as described in section 1. After 5 days of culture, supernatants harvested from the culture of transiently transfected cells were used for protein purification. The benchmark antibodies were purified from the supernatants.

3. Establishment of Stable Cell Lines

Human, mouse and cynomolgus LAG-3 transfectant cell lines were generated. Briefly, Flp-In-293, Flp-In-CHO or 293F cells were transfected with pcDNA3.3 expression vector containing full-length of human, mouse and cynomolgus LAG-3 using Lipofectamine 2000 transfection kit according to manufacturer's protocol, respectively. At 48-72 hours post transfection, the transfected cells were cultured in medium containing blasticidin for selection and tested for LAG-3 expression. Human LAG-3-expressing cell lines, cynomolgus monkey LAG-3-expressing cell lines, and mouse LAG-3 expressing cell lines were obtained by limiting dilution.

Example 2

Antibody Hybridoma Generation

1. Immunization and cell fusion

OMT rats (transgenic rats having recombinant immunoglobulin loci, as described and produced in U.S. Pat. No. 8,907,157 B2), 24 weeks of age, were immunized with 12.5 µg of hFc-tagged human LAG-3 ECD protein and 12.5 µg of His-tagged mouse LAG-3 in adjuvant alternately, producing antibodies in which both the framework and CDR regions are derived from human germline immunoglobulin sequences. The immunized rats were bled every two weeks for serum collection and titers against human LAG-3 in the serum were measured by ELISA. The 96-well plates coated with human LAG-3.ECD.hFc were co-incubated with diluted rat serum (first 1:100, then 3-fold dilution in 2% BSA) for two hours. Goat anti rat-IgG-Fc-HRP was used as secondary antibody. The color was developed by dispensing 100 µL of TMB substrate, and then stopped by 100 µL of 2N HCl. The absorbance was read at 450 nM using a microplate reader. Once the antibody titer reached sufficiently high, rats were given a final boost with 40 µg of human LAG-3 ECD protein in DPBS without adjuvant. On the day of fusion, lymph nodes and spleen were removed from immunized rats under sterile condition, and prepared into single cell suspension. The isolated cells were then mixed with myeloma cell SP2/0 at a ratio of 1:1. Electro cell fusion was performed using BTX 2000 Electro cell manipulator. The cells were then seeded in 96-well plates at the density of $1 \times 10^4$ cells/well, and cultured at 37° C., 5% $CO_2$, until ready for screening.

2. Primary and Confirmatory Screening of Hybridoma Supernatants

ELISA assay was used as the first screening method to test the binding of hybridoma supernatants to LAG-3 protein. Plates in section 1 of this Example were coated with human LAG-3 ECD.hFc at 1 µg/mL overnight at 4° C. After blocking and washing, the hybridoma supernatants were transferred to the coated plates and incubated at room temperature for 1 h. The plates were then washed and subsequently incubated with secondary antibody goat anti-rat IgG HRP for 1 h. After washing, TMB substrate was added and the color reaction was stopped by 2M HCl. The absorbance at 450 nm was read using a microplate reader.

In order to confirm the native binding of LAG-3 antibodies to conformational LAG-3 molecules expressed on cell membrane, flow cytometry analysis was performed on LAG-3 transfected CHO-K1 cell line. CHO-K1 cells expressing human LAG-3 were transferred into 96-well U-bottom plates at a density of $1 \times 10^5$ cells/well. The hybridoma supernatants were then transferred to the plates and incubated for 1 h at 4° C. After washing with 1×PBS/1% BSA, the secondary antibody goat anti-rat IgG Alexa647 was added and incubated with cells at 4° C. in the dark for 0.5 h. The cells were then washed and resuspended in 1×PBS/1% BSA before being analyzed by flow cytometry. The binding of antibodies to parental CHO-K1 cell line was performed in parallel as negative controls.

The blocking activities of antibodies were used as confirmatory screening to select potential antibody hits. Selected antibodies were tested for the ability to block the binding of LAG-3 protein to human MHC-II expressing cell line Raji by FACS analysis. Raji cells were transferred into 96-well U-bottom plates at the density of $1 \times 10^5$ cells/well. The supernatant was incubated with mFc-tagged LAG-3 protein at 4° C. for 30 min. The mixture was transferred into the 96-well plates seeded with Raji cells. The secondary antibody, PE-labeled goat anti-mouse-IgG antibody (no cross-reactivity to rat IgG Fc, Jackson Immunoresearch Lab) was incubated with cells at 4° C. in the dark for 0.5 h. The cells were then washed and resuspended in 1×PBS/1% BSA and analyzed by flow cytometry.

3. Hybridoma Sub-Cloning:

Once specific binding was verified through primary and confirmatory screening, the positive hybridoma cell lines were sub-cloned to get monoclonal anti-hLAG-3 antibodies by using semi-solid medium approach. In the semi-solid medium approach, for each hybridoma cell line, cells were diluted in semi-solid cloning medium (STEMCELL Technologies) and seeded in 6-well plates. The cells were cultured for 8-10 days in an incubator (37° C., 5% $CO_2$) until monoclones were visible in semi-solid medium. Clones were picked and transferred to 96-well plate in HAT medium (hypoxanthine-aminopterin-thymidine medium) with 10% FBS. The positive clones were confirmed by binding ELISA and FACS against human LAG-3 as described above.

Example 3

Hybridoma Sequencing and Fully Human Antibody Molecules Construction

1. Hybridoma sequencing

Total RNA was extracted from hybridoma cells by using RNeasy Plus Mini Kit (Qiagen) and first strand cDNA was prepared as shown in Table 1 and Table 2. Antibody VH and VL genes were amplified from cDNA as shown in Table 3 and Table 4 by using 3'-constant region degenerated primer and 5'-degenerated primer sets, which are complementary to the upstream signal sequence-coding region of Ig variable sequences. Reagent information including the manufactures is shown in Table 5.

The PCR product (10 µL) was ligated into pMD18-T vector and 10 µL of the ligation product was transformed into Top10 competent cells. Transformed cells were plated on 2-YT+Cab plates and incubated overnight at 37° C. Positive clones were randomly picked for sequencing at Shanghai Biosune Biotech Co., Ltd.

TABLE 1

| cDNA amplification reaction (20 µL) | |
|---|---|
| Component | Amount |
| Up to 5 µg total RNA | 5 µL |
| Primer (50 µM oligo(dT)$_{20}$/50 ng/µL random hexamers) | 1 µL/1 µL |
| Annealing Buffer | 1 µL |
| RNase/DNase-free water | to 8 µL |
| 65° C. for 5 min, then immediately place on ice for at least 1 minute | |
| 2 × First-Strand Reaction Mix | 10 µL |
| SuperScript ™ III/RNaseOUT ™ Enzyme Mix | 2 µL |

TABLE 2

| cDNA amplification reaction condition | | | | |
|---|---|---|---|---|
| | Step 1 | Step 2 | Step 3 | Step 4 |
| Temperature (° C.) | 25 | 50 | 85 | 4 |
| Time | 10 min | 50 min | 5 min | ∞ |

TABLE 3

| PCR Reaction system (50 µL) | |
|---|---|
| Component | Amount |
| CDNA | 2.0 µL |
| Premix Ex Taq | 25 µL |
| 5'-degenerated primer sets (10 pM) | 2.5 µL |
| 3'-constant region degenerated primer (10 pM) | 1 µL |
| ddH$_2$O | 19.5 µL |

TABLE 4

| PCR Reaction condition | | | | | |
|---|---|---|---|---|---|
| | Step 1 | Step 2 | Step 3 | Step 4 | Step 5 |
| Temperature (° C.) | 95 | 94 | 58 | 72 | 72 |
| Time | 4 min | 45 sec | 45 sec | 1 min | 10 min |
| Cycles | NA | 30 | | NA | NA |

TABLE 5

| Reagent information | |
|---|---|
| Reagent | Manufacturers |
| RNeasy Plus Mini Kit | QIAGEN |
| SuperScript III First-Strand Synthesis SuperMix | Invitrogen |
| Premix Ex Taq hot start | TaKaRa |
| DNA Gel Extraction Kit | Axygen |
| pMD 18-T vector | TaKaRa |

Two lead antibodies are named as "1.53.3-uAb-IgG4k" and "3.40.19-uAb-IgG4L", respectively.

The sequences of CDRs of 1.53.3-uAb-I2G4k were determined as follows:

| Description | SEQ ID NO. | Sequence Information |
|---|---|---|
| CDRH1 | 1 | GGSFSGYYWS |
| CDRH2 | 2 | EINHRGNTNYNPSLKS |
| CDRH3 | 3 | GEDYSDYDYYGDF |
| CDRL1 | 4 | RASQSISSYLA |
| CDRL2 | 5 | AASNRAT |
| CDRL3 | 6 | QQRSNWPLT |

The sequences of heavy chain and light chain variable regions of 1.53.3-uAb-IgG4k are as follows:

| Description | SEQ ID NO. | Sequence Information |
|---|---|---|
| VH | 13 | QVQLQQWGAGLLKPSETLSLTCGVYGGSFSGYYW SWIRQPPGMGLEWIGEINHRGNTNYNPSLKSRVTIS EDTSKNQFSLRLSSVTAADTAVYFCTRGEDYSDYD YYGDFWGQGTLVTVSS |
| VL | 14 | EIVLTQSPATLSLSQGERATLSCRASQSISSYLAWY QQKPGQAPRLLIYAASNRATGIPARFSGSGSGTDFT LTISSLEPEDFAIYYCQQRSNWPLTFGGGTKVEIK |

The sequences of CDRs of 3.40.19-uAb-IgG4L are as follows:

| Description | SEQ ID NO. | Sequence Information |
|---|---|---|
| CDRH1 | 7 | GDSISSTSYYWG |
| CDRH2 | 8 | SFYYSGSTYYNPSLKS |
| CDRH3 | 9 | MQLWSYDVDV |
| CDRL1 | 10 | TGTSSDVGGYDYVA |
| CDRL2 | 11 | DVSERPS |
| CDRL3 | 12 | SSYTSTTTLVV |

The sequences of heavy chain and light chain variable regions of 3.40.19-uAb-IgG4L are as follows:

| Description | SEQ ID NO. | Sequence Information |
|---|---|---|
| VH | 15 | QLQLQESGPGLVKPSETLSLTCTVSGDSISSTSYY WGWIRQPPGKGLEWIGSFYYSGSTYYNPSLKSR VTISVDTSKNQFSLKLNSVTAADTAVYYCARMQ LWSYDVDVWGQGTTVTVSS |
| VL | 16 | QSALTQPASVSGSPGQSITISCTGTSSDVGGYDY VAWYQQHPGKVPKLMIYDVSERPSGVSNRFSGS KSGNTASLTISGLQAEDEADYYCSSYTSTTTLVV FGGGTKLSVL |

2. Fully Human Antibody Molecule Construction

VH and VL genes were re-amplified with cloning primers containing appropriate restriction sites and cloned into expression vectors to create corresponding clones of chimeric antibodies.

Example 4

Binding of LAG-3 Antibodies to Cell Surface Human LAG-3

Various concentrations of testing antibodies, positive and negative controls were added to human LAG-3 transfectant cells, and then the binding of antibodies onto the surface of the cells was detected by corresponding PE-labeled secondary antibodies. The data was shown in FIG. 1 and $EC_{50}$ was shown in Table 6.

TABLE 6

| Ab | $EC_{50}$ (nM) |
| --- | --- |
| 1.53.3-uAb-IgG4k | 0.43 |
| 3.40.19-uAb-IgG4L | 0.13 |
| BMK1 | 0.32 |
| BMK7 | 0.61 |
| BMK8 | 0.90 |

As shown in FIG. 1 and Table 6, surprisingly, the $EC_{50}$ of 3.40.19-uAb-IgG4L (0.13) for binding to cell surface LAG-3 is significantly lower than that of all the three benchmark antibodies BMK1(0.32), BMK7 (0.61) and BMK8 (0.90). Further, the $EC_{50}$ of 1.53.3-uAb-IgG4k (0.43) for binding to cell surface LAG-3 is much lower that of BMK7 (0.61) and BMK8 (0.90). These results indicate that 1.53.3-uAb-IgG4k and 3.40.19-uAb-IgG4L are effective in binding to human LAG-3, and the binding effects are superior over or comparable to the benchmark antibodies.

Example 5

Blocking of LAG-3 Protein Binding to MHC-II Expressed on Raji Cells

Antibodies were serially diluted in 1% BSA-PBS and incubated with mFc-tagged LAG-3 protein at 4° C. for 30 min. The mixture was transferred into the 96-well plates seeded with Raji cells. Goat anti-mouse IgG Fc-PE antibody was used to detect the binding of LAG-3 protein to Raji cells. The MFI was evaluated by flow cytometry and analyzed by the software FlowJo (version 7.6.1). The data was shown in FIG. 2 and $EC_{50}$ was shown in Table 7.

TABLE 7

| Ab | $EC_{50}$ (nM) |
| --- | --- |
| 1.53.3-uAb-IgG4k | 0.80 |
| 3.40.19-uAb-IgG4L | 0.67 |
| BMK1 | 0.76 |
| BMK7 | 1.25 |
| BMK8 | 0.88 |

Figure 2:
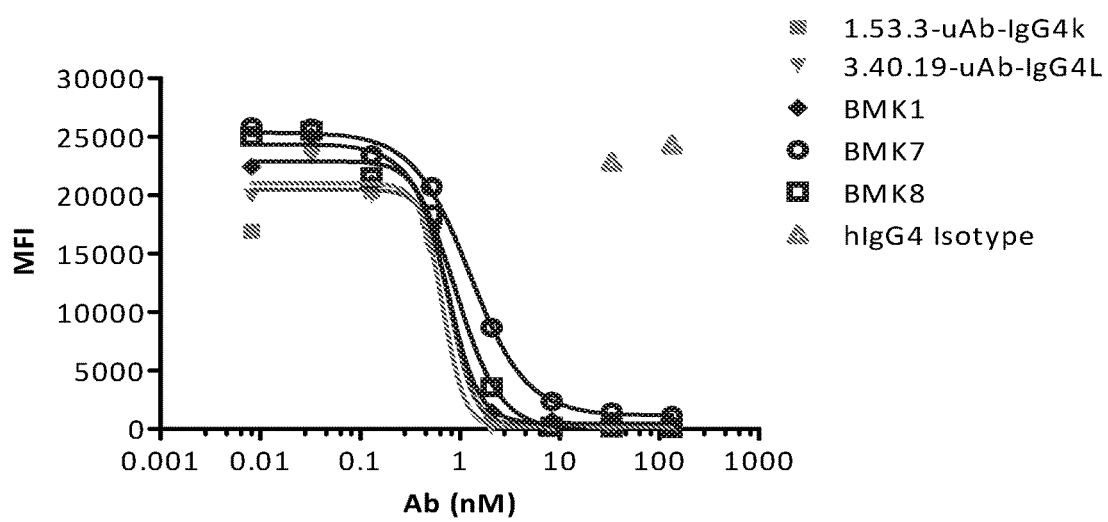
FIG. 2 shows the blocking of LAG-3 protein binding to MHC-II expressed on Raji cells.

As shown in FIG. 2 and Table 7, surprisingly, the $EC_{50}$ of 3.40.19-uAb-IgG4L (0.67) for binding to MHC-II expressed on Raji cells is significantly lower than that of all the three benchmark antibodies BMK1(0.76), BMK7 (1.25) and BMK8 (0.88). Further, the EC50 of 1.53.3-uAb-IgG4k (0.80) for binding to MHC-II expressed on Raji cells is lower that of BMK7 (1.25) and BMK8 (0.88). These results indicate that 1.53-uAb-IgG4k and 3.40.19-uAb-IgG4L are effective in blockage of the binding to MHC-II expressed on Raji cells, and the blocking effects are superior over or comparable to the benchmark antibodies.

Example 6

Blocking of LAG-3 protein binding to LSECtin and Galectin-3

96-well plates were coated with human LSECtin or Galectin-3 at 0.5 μg/mL overnight at 4° C., respectively. Antibodies were serially diluted in 1% BSA-PBS and mixed with mFc-tagged LAG-3 protein. After blocking and washing, the mixture was transferred to the plates and incubated at room temperature for 1 h. The plates were then washed and subsequently incubated with corresponding secondary antibody for 60 min. After washing, TMB substrate was added and the color reaction was stopped by 2M HCl. The absorbance at 450 nm was read using a microplate reader. The data was shown in FIGS. 3 and 4. $EC_{50}$ was shown in Table 8.

TABLE 8

| | $EC_{50}$ (nM) | |
| --- | --- | --- |
| Ab | LSECtin blocking | Galectin-3 blocking |
| 1.53.3-uAb-IgG4k | 0.71 | 0.74 |
| 3.40.19-uAb-IgG4L | 0.51 | 0.56 |
| BMK1 | 0.68 | 0.63 |
| BMK7 | 0.59 | 0.79 |
| BMK8 | 1.06 | 1.07 |

Figure 3:
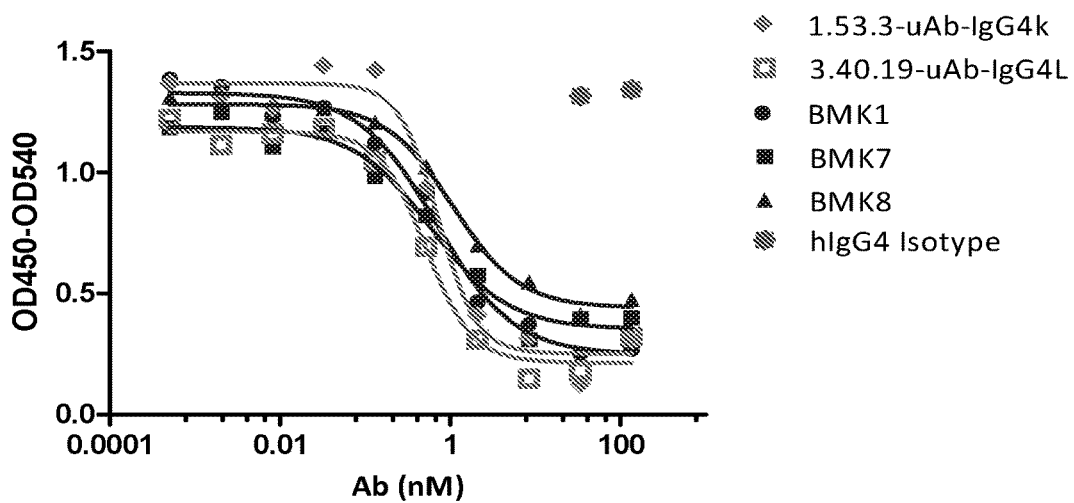
FIG. 3 shows the blocking of LAG-3 protein binding to LSECtin.
Figure 4:
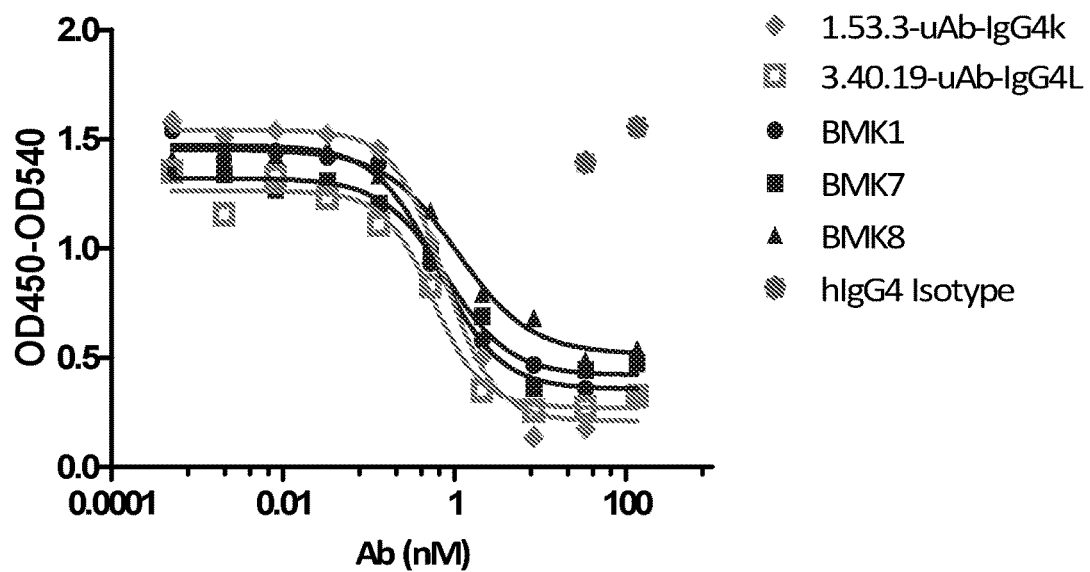
FIG. 4 shows the blocking of LAG-3 protein binding to Galectin-3.

As shown in FIGS. 3 and 4 as well as Table 7, both 1.53.3-uAb-IgG4k and 3.40.19-uAb-IgG4L are effective in blocking the binding of LAG-3 to LSECtin or Galectin-3, and the blocking effects are superior over or comparable to the benchmark antibodies.

Example 7

Full Kinetic Binding Affinity Test

Full Kinetic Binding Affinity Tested by Surface Plasmon Resonance (SPR):

Antibodies were characterized for affinity and binding kinetics to human LAG-3 by SPR assay using Biacore 8K. Goat anti-human Fc was pre-immobilized to a sensor chip (CM5), and anti-LAG-3 antibodies were captured when injected to the chip. Various concentrations of human LAG-3 protein and running buffer were flowed through the sensor chip at a flow rate of 30 μL/min for an association phase of 300 s, followed by 3600 s dissociation. The association and dissociation curve was fit by 1:1 Langmuir binding model using Biacore 8K Evaluation Software. The data was shown in Table 9.

TABLE 9

| Ab | ka (1/Ms) | kd (1/s) | KD (M) |
| --- | --- | --- | --- |
| 1.53.3-uAb-IgG4k | 6.60E+05 | 3.33E−05 | 5.05E−11 |
| 3.40.19-uAb-IgG4L | 1.05E+06 | 1.11E−05 | 1.06E−11 |
| BMK1 | 4.87E+05 | 3.34E−04 | 6.85E−10 |
| BMK7 | 2.13E+05 | 1.06E−04 | 4.97E−10 |
| BMK8 | 8.46E+04 | 6.74E−06 | 7.97E−11 |

Binding Affinity of LAG-3 Antibodies to Cell Surface LAG-3 Molecules Tested by Fluorescence-Activated Cell Sorting (FACS)

Antibody binding affinity to cell surface LAG-3 was measured by FACS analysis. Flp-In-293 cells expressing human LAG-3 were transferred in to 96-well U-bottom plates at a density of $5\times10^5$ cells/mL. Tested antibodies were serially diluted in wash buffer (1×PBS/1% BSA) and incubated with cells at 4° C. for 1 h. The secondary antibody goat anti-human IgG Fc FITC (3.5 moles FITC per mole IgG) was added and incubated at 4° C. in the dark for 0.5 h. The cells were then washed once and resuspended in 1×PBS/1% BSA, and analyzed by flow cytometry. Fluorescence intensity will be converted to bound molecules/cell based on the quantitative beads (Quantum™ MESF Kits, Bangs Laboratories, Inc.). Affinity was calculated using Graphpad Prism 5. The data was shown in table 10.

TABLE 10

| Ab | KD (M) |
| --- | --- |
| 1.53.3-uAb-IgG4k | 1.60E−10 |
| 3.40.19-uAb-IgG4L | 5.30E−11 |
| BMK1 | 2.70E−10 |
| BMK7 | 5.80E−10 |
| BMK8 | 9.40E−10 |

As tested by SPR and FACS, the antibodies of the disclosure, as represented by 1.53.3-uAb-IgG4k and 3.40.19-uAb-IgG4L, are effective in binding to human LAG-3, and the binding effects are superior over or comparable to the benchmark antibodies.

Example 8

Orthologue (Cross-Species) and Homologue (Cross-Family) Binding
Cross-Reactivity to Cynomolgus LAG-3 and Murine LAG-3

Cross-reactivity to cynomolgus and murine LAG-3 was measured by FACS. Murine LAG-3-expressing Flp-In-CHO cells or cynomolgus LAG-3-expressing 293F cells were transferred into 96-well U-bottom plates at a density of 1×10$^5$ cells/well. Testing antibodies were serially diluted in wash buffer (1×PBS/1% BSA) and incubated with cells at 4° C. for 1 h. After washing with 1×PBS/1% BSA, corresponding secondary antibody was applied and incubated with cells at 4° C. in the dark for 1 h. The cells were then washed and resuspended in 1×PBS/1% BSA and then analyzed by flow cytometry. The data was shown in FIG. 5 and FIG. 6. EC$_{50}$ was shown in Table 11.

TABLE 11

| Ab | EC$_{50}$ (nM) |
| --- | --- |
| 1.53.3-uAb-IgG4k | 4.01 |
| 3.40.19-uAb-IgG4L | 3.92 |
| BMK1 | 86.0 |
| BMK7 | 2.65 |
| BMK8 | 3.05 |

Figure 5:
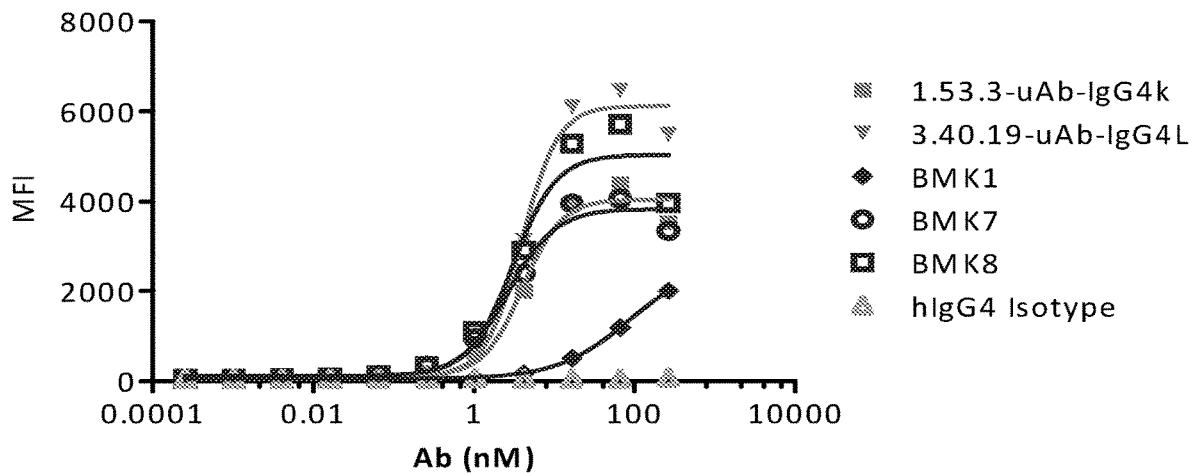
FIG. 5 shows cross-reactivity to cynomolgus LAG-3 as measured by FACS.
Figure 6:
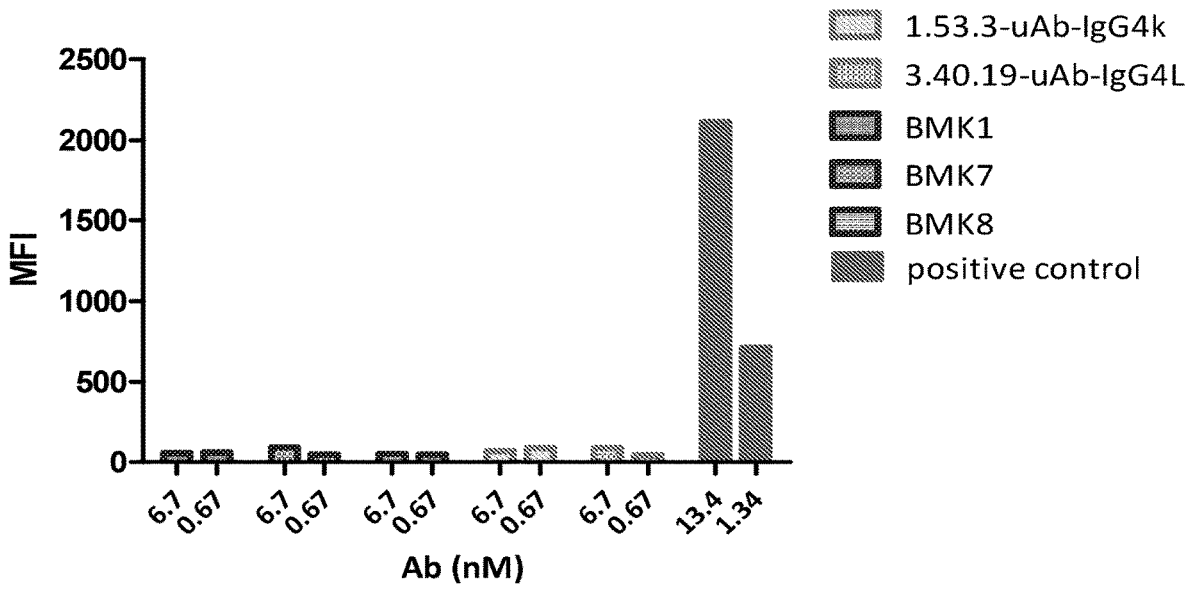
FIG. 6 shows cross-reactivity to murine LAG-3 as measured by FACS.

As demonstrated in FIG. 5, LAG-3 antibodies of the disclosure "1.53.3-uAb-IgG4k" and "3.40.19-uAb-IgG4L" bound to cell surface cynomolgus LAG-3. And as demonstrated in FIG. 6, LAG-3 antibodies of the disclosure "1.53.3-uAb-IgG4k" and "3.40.19-uAb-IgG4L" did not bind to cell surface mouse LAG-3.

Cross-Reactivity to Human CD4

Figure 7:
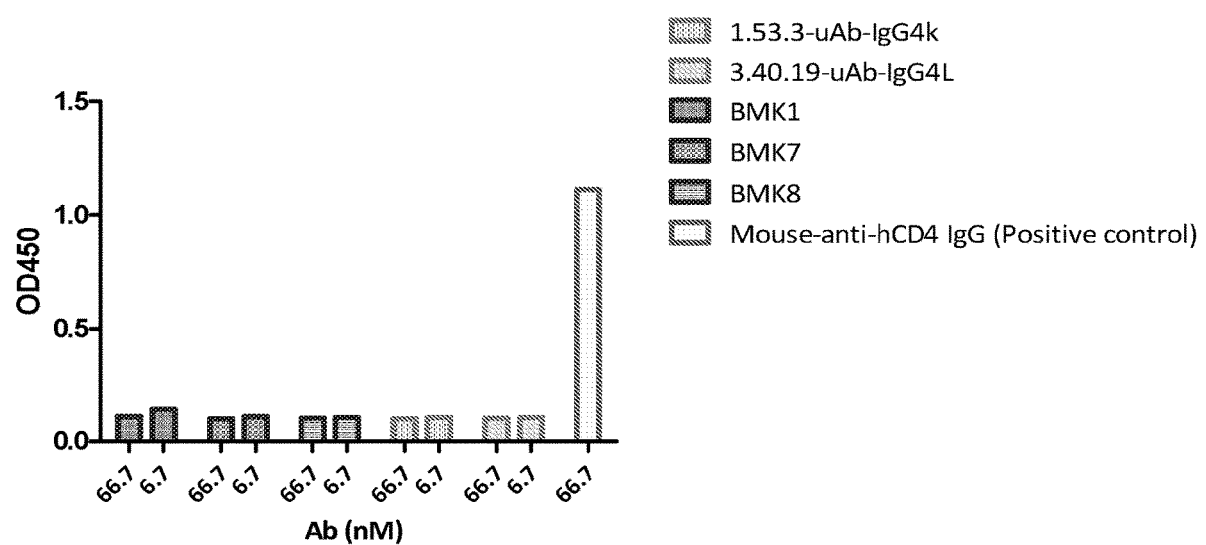
FIG. 7 shows cross-reactivity to human CD4 as measured by ELISA.
Figure 8A:
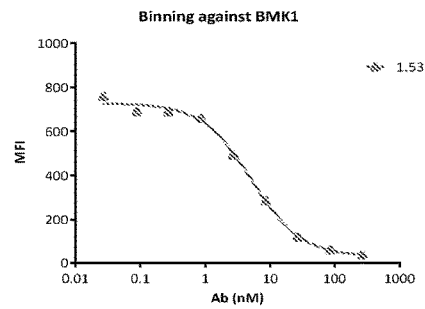
FIG. 8A-E shows epitope binning against benchmark antibodies BMK1, BMK7 and BMK5.
Figure 8B:
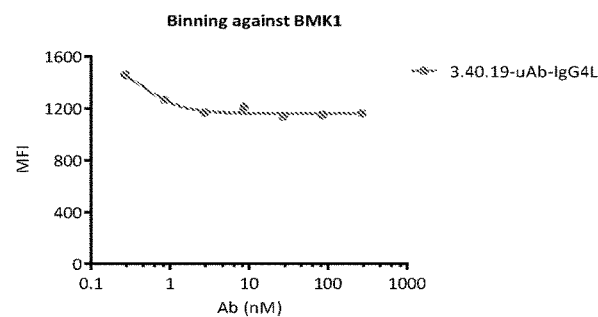
Figure 8C:
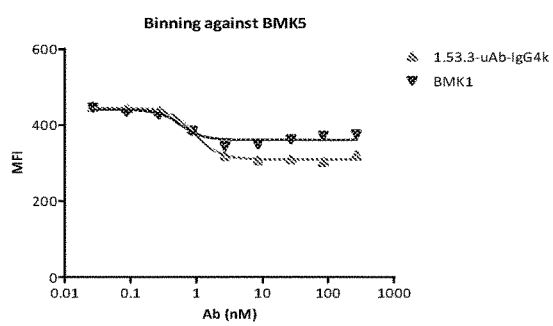
Figure 8D:
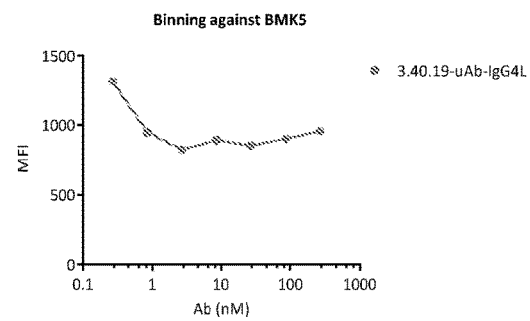
Figure 8E:
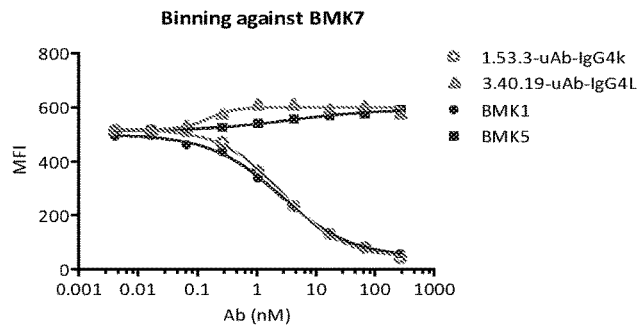

Cross-reactivity to human CD4 was measured by ELISA. Plates were coated with human CD4 at 1 μg/mL overnight at 4° C. After blocking and washing, 1 μg/mL of LAG-3 antibodies were added to the plates and incubated at room temperature for 1 h. The plates were then washed and subsequently incubated with corresponding secondary antibody for 45 min. After washing, TMB substrate was added and the color reaction was stopped by 2M HCl. The absorbance at 450 nm was read using a microplate reader. The data was shown in FIG. 7.

These results indicate that LAG-3 antibodies of the disclosure "1.53.3-uAb-IgG4k" and "3.40.19-uAb-IgG4L" did not bind to human CD4 protein.

Example 9

Epitope Binning Against BMK1, BMK7 and BMK5

The binding epitope of LAG-3 antibodies was binned against benchmark antibodies BMK1, BMK7 and BMK5 by FACS assay. Flp-In-293 cells expressing human LAG-3 at the cell surface were incubated with biotinylated benchmark antibodies at concentration of 1 μg/mL for 1 hour, followed by the adding of serially diluted LAG-3 antibodies. Streptavidin-PE antibody (Jackson Immunoresearch Lab) was used to detect the binding of benchmark antibodies to cells. The MFI was evaluated by flow cytometry and analyzed by FlowJo. The data was shown in FIG. 8A-E.

It was found that 1.53.3-uAb-IgG4k of the disclosure competed with BMKs, but 3.40.19-uAb-IgG4L did not compete with BMKs. 1.53.3-uAb-IgG4k shares close epitope with BMK1 and BMK7, but not BMK5. Surprisingly, 3.40.19-uAb-IgG4L has different epitope with all of BMK1, BMK7 and BMK5.

Example 10

Domain Mapping and Epitope Mapping
1. Domain Mapping

LAG-3 has an extracellular domain of 421 aa (P30-L450) including four extracellular immunoglobulin superfamily (IgSF)-like domains, namely Domain 1 ("D1," aa. 37-167), Domain 2 ("D2," aa 168-252), Domain 3 ("D3," aa. 265-343) and Domain 4 ("D4," aa. 348-419). 10 variants as follows were constructed by replacing the following residues of the extracellular domain of human LAG-3 with corresponding mouse LAG-3 amino acid (also referred to as "aa" in the context of the disclosure).

(1) Variant 1: xProl.FL-x1: Human LAG-3 aa 168 to 419 replaced with the mouse counterparts
(2) Variant 2: xProl.FL-x2: Human LAG-3 aa 37 to 167, and aa 265 to 419 replaced with the mouse counterparts
(3) Variant 3: xProl.FL-x3: Human LAG-3 aa 37 to 252, and aa 348-419 replaced with the mouse counterparts
(4) Variant 4: xProl.FL-x4: Human LAG-3 aa 37 to 343 replaced with the mouse counterparts
(5) Variant 5: xProl.FL-x5: Human LAG-3 aa 265 to 419 replaced with the mouse counterparts
(6) Variant 6: xProl.FL-x6: Human LAG-3 aa 37 to 167, and aa 348 to 419 replaced with the mouse counterparts
(7) Variant 7: xProl.FL-x7: Human LAG-3 aa 37 to 252 replaced with the mouse counterparts
(8) Variant 8: xProl.FL-x8: Human LAG-3 aa 168 to 343 replaced with the mouse counterparts
(9) Variant 9: xProl.FL-x9: Human LAG-3 aa 348 to 419 replaced with the mouse counterparts
(10) Variant 10: xProl.FL-x10: Human LAG-3 aa 37 to 167 replaced with the mouse counterparts The 10 variants were cloned into pcDNA3 vector and used for 293F cell transfection. Briefly, 293F cells were diluted to a density of 1×10$^6$ cells/mL with FreeStyle 293F medium and aliquots of 3 mL/well were added to 24-well plate. Transfections were performed using 293fectin reagent (Life Technologies). For each transfection, 3 μg of DNA were diluted in 150 μL Opti-MEM I-reduced serum medium (Life Technologies), and then combined with 6 μL 293fectin reagent pre-diluted in 150 μL Opti-MEM I reduced serum medium. The DNA/Lipofectamine mixture was allowed to stand at 25° C. for 20 min before being added to the culture. The transfected cells were analyzed by flow cytometry at 48 h post-transfection.

Binding of antibodies to chimeric LAG-3 variants or full length human/mouse LAG-3 was analyzed by flow cytometry. Briefly, 1 μg/mL antibodies were incubated with chimeric LAG-3-expressing transfected 293F cells for 1 hour at 4° C., and then incubated with 3 μg/mL goat anti-human IgG Fc R-PE (Jackson) for 40 min at 4° C. Cells were analyzed with flow cytometer.

The binding abilities of the antibodies 1.53.3-uAb-IgG4k and 3.40.19-uAb-hIgG4L to the 10 variants were tested and the results were shown in Table 12 below.

TABLE 12

The binding MFI value of LAG-3 antibodies on 10 variants

| Antigen variant | 1.53.3-uAb-IgG4k | | 3.40.19-uAb-hIgG4L | |
| --- | --- | --- | --- | --- |
| | MFI | PE+ % | MFI | PE+ % |
| Variant 1 | 8582 | 97 | 9428 | 89.4 |
| Variant 2 | 45 | 1.77 | 40.6 | 0.305 |
| Variant 3 | 41.7 | 2.03 | 54 | 0.426 |
| Variant 4 | 41 | 1.42 | 41.7 | 0.658 |
| Variant 5 | 6260 | 97.1 | 7070 | 75.9 |
| Variant 6 | 59.9 | 1.86 | 44.1 | 0.674 |
| Variant 7 | 39.3 | 1.52 | 44.3 | 0.859 |
| Variant 8 | 7432 | 97.6 | 5236 | 70.1 |
| Variant 9 | 7030 | 97.3 | 8317 | 87.3 |
| Variant 10 | 42.3 | 1.98 | 68.5 | 0.988 |
| hPro1.FL (SEQ ID NO: 23) | 6539 | 96.8 | 6517 | 83.5 |
| mPro1.FL (SEQ ID NO: 25) | 43.9 | 1.1 | 34.5 | 0.252 |
| Blank | 29.4 | 0 | 29.4 | 0 |
| Negative control | 30.6 | 0.656 | 29.4 | 0.1 |

According to the FACS binding activity of antibodies, both two lead antibodies "1.53.3-uAb-IgG4k" and "3.40.19-uAb-hIgG4L" bound to Domain 1 (i.e. aa. 37-167). So further epitope mapping of Domain 1 (G37-Q167, 131 aa) was performed by alanine scanning experiments.

2. Epitope Mapping

Alanine scanning experiments on human LAG-3 were conducted for epitope mapping. Alanine residues on human LAG-3 were mutated to glycine codons, and all other residues (except for cysteine residues) were mutated to alanine codons. For each residue of the human LAG-3 extracellular domain (ECD), site amino acid substitutions were made using two sequential PCR steps. A pcDNA3.3-LAG-3-D12.mFc plasmid that encodes ECD domain 1 and domain 2 of human LAG-3 and a C-terminal mFc-tag was used as template, and a set of mutagenic primers was used for first step PCR using the QuikChange lightning multisite-directed mutagenesis kit (Agilent technologies, Palo Alto, CA). Dpn I endonuclease was used to digest the parental template after mutant strand synthesis reaction. In the second-step PCR, linear DNA expression cassette which composed of a CMV promoter, extracellular domain 1 and domain 2 (D1 and D2) of LAG-3, a mFc-tag and a herpes simplex virus thymidine kinase (TK) polyadenylation was amplified and transiently expressed in Expi293 cells at 37° C. (Life Technologies, Gaithersburg, MD), quantified by Protein A-HPLC and mFc-ELISA quantification Kit (Bethyl, USA).

For ELISA binding assay, the antibody 1.53.3-uAb-IgG4k or 3.40.19-uAb-hIgG4L (2 μg/mL) was coated in plates. After interacting with the supernatant that contains quantified LAG-3 mutants or human LAG-3-ECD.D12.mFc protein, HRP conjugated anti-mFc antibody (1:5000; Bethyl, USA) was added as a detection antibody. Absorbance was normalized according to the average absorbance of control mutants. After setting an additional cutoff to the binding fold change (<0.75), the final determined epitope residues were identified. The hotspots of the antibodies 1.53.3-uAb-IgG4k and 3.40.19-uAb-hIgG4L were shown in Table 13 and Table 14.

TABLE 13

Hotspots of 1.53.3-uAb-IgG4k antibody

| Residue | | Fold Change |
| --- | --- | --- |
| G | 37 | 0.558 |
| L | 42 | 0.624 |
| A | 59 | 0.718 |
| V | 61 | 0.637 |
| W | 63 | 0.585 |
| H | 65 | 0.627 |
| P | 72 | 0.743 |
| W | 92 | 0.554 |
| V | 101 | 0.504 |
| L | 122 | 0.607 |
| A | 139 | 0.708 |
| D | 143 | 0.671 |
| G | 145 | 0.692 |
| E | 146 | 0.701 |
| Y | 147 | 0.637 |
| L | 153 | 0.749 |
| L | 164 | 0.586 |

TABLE 14

Hotspots of 3.40.19-uAb-IgG4L antibody

| Residue | | Fold Change |
| --- | --- | --- |
| G | 37 | 0.284 |
| A | 40 | 0.608 |
| L | 42 | 0.306 |
| P | 43 | 0.494 |
| A | 59 | 0.542 |
| V | 61 | 0.514 |
| T | 62 | 0.727 |
| W | 63 | 0.171 |
| H | 65 | 0.489 |
| T | 100 | 0.738 |
| V | 101 | 0.275 |
| L | 122 | 0.391 |
| G | 130 | 0.102 |
| D | 131 | 0.045 |
| L | 134 | 0.040 |
| W | 135 | 0.049 |
| L | 136 | 0.043 |
| R | 137 | 0.101 |
| P | 138 | 0.106 |
| A | 139 | 0.368 |
| D | 143 | 0.529 |
| G | 145 | 0.466 |
| E | 146 | 0.582 |
| Y | 147 | 0.190 |
| V | 151 | 0.043 |
| L | 153 | 0.632 |
| D | 155 | 0.701 |
| R | 163 | 0.655 |
| L | 164 | 0.278 |

Figure 9A:
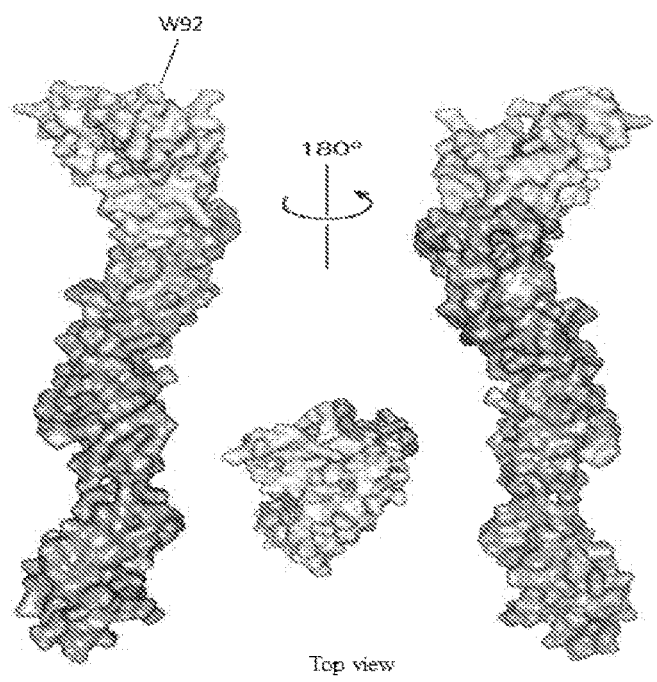

As no existed LAG-3 structure, the structure of the LAG-3 (aa: 31-431) was modeled based on the known structure of the myelin-associated glycoprotein (PDB:

5FLU, sequence identity 18%). Based on alanine scanning results, hotspots of two antibodies were identified and shown in FIG. 9A and FIG. 9B.

Based on the results, it can be seen that the 1.53.5-uAb-IgG4k antibody bound to W92 site which belongs to the extra loop (G70-Y99), while the 3.40.19-uAb-IgG4L antibody bound to L134-P138 region.

Example 11

In Vitro Function of LAG-3 Antibodies Tested by Cell-Based Assays
Effects of Human LAG-3 Antibodies in Reporter Gene Assay Jurkat cells expressing human LAG-3 along with stably integrated IL-2 luciferase reporter gene were seeded in 96-well plates along with Raji cells in the presence of SEE. Testing antibodies were added to the cells. The plates were incubated for overnight at 37° C., 5% $CO_2$. After incubation, reconstituted luciferase substrate was added and the luciferase intensity was measured by a microplate spectrophotometer. The data was shown in FIG. 10 and EC50 was shown in Table 15.

TABLE 15

| Ab | $EC_{50}$ (nM) |
|---|---|
| 1.53.3-uAb-IgG4k | 1.07 |
| 3.40.19-uAb-IgG4L | 0.21 |
| BMK1 | 0.59 |
| BMK7 | 2.65 |
| BMK8 | 65.3 |

Figure 10:
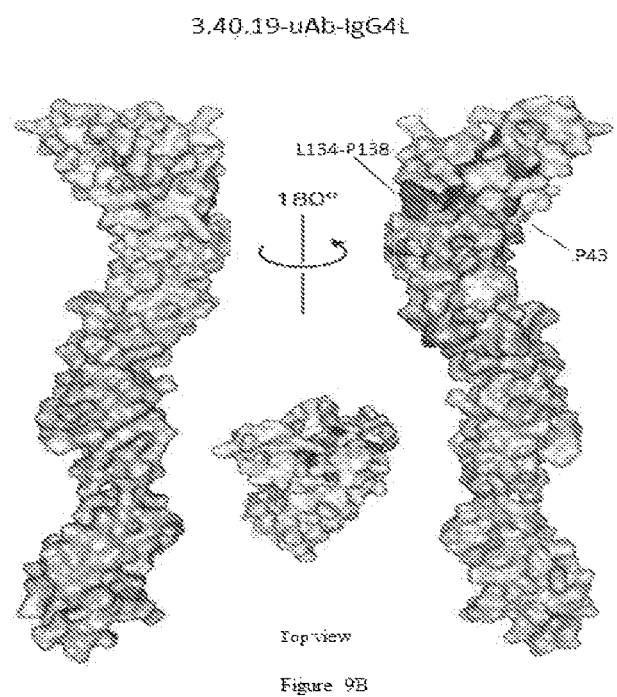
FIG. 10 shows the effects of human LAG-3 antibodies in reporter gene assay.
Figure 10:
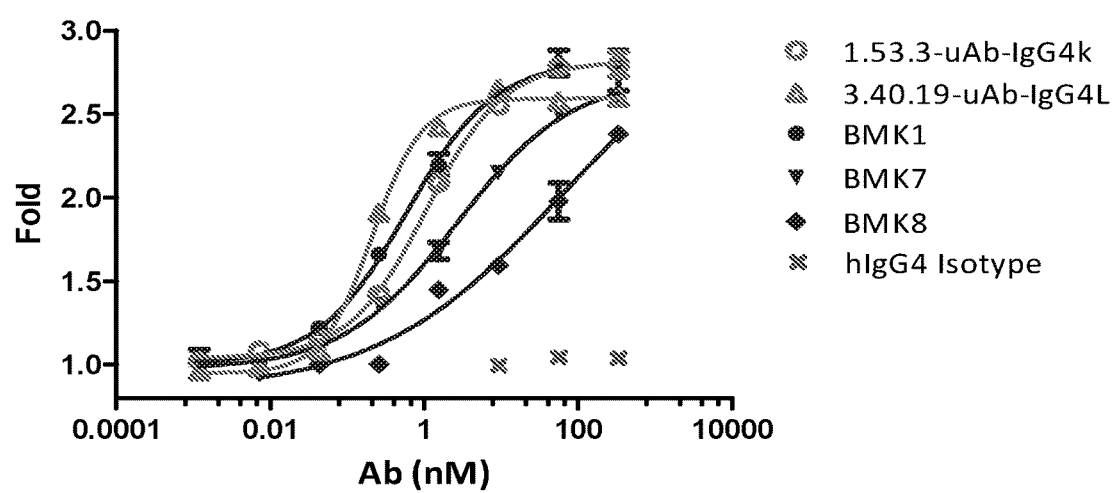

As demonstrated in FIG. 10, LAG-3 antibodies enhanced IL-2 pathway of Jurkat in reporter gene assay. Further, as shown in Table 15, the EC50 of 3.40.19-uAb-IgG4L in this assay is significantly lower than all of the three benchmark antibodies.

Effects of Human LAG-3 Antibodies on Human Allogeneic Mixed Lymphocyte Reaction

Human peripheral blood mononuclear cells (PBMCs) were freshly isolated from healthy donors using Ficoll-Paque PLUS gradient centrifugation. Monocytes were isolated using human monocyte enrichment kit according to the manufacturer's instructions. Cells were cultured in medium containing GM-CSF and IL-4 for 5 to 7 days to generate dendritic cells (DC). Human $CD4^+$ T cells were isolated using human $CD4^+$ T cell enrichment kit according to the manufacturer's protocol. Purified $CD4^+$ T cells were co-cultured with allogeneic immature DCs (iDCs) and various concentrations of LAG-3 antibodies in 96-well plates. On Day 5, the culture supernatants were harvested for IFN-γ test and T cell proliferation test. Human IFN-γ was measured by ELISA using matched antibody pairs. The plates were pre-coated with capture antibody specific for human IFN-γ (Pierce-M700A). The biotin-conjugated anti-IFN-γ antibody (Pierce-M701B) was used as detecting antibody. During the last 16 h, $^3$H-thymidine was added at 1 μCi/well. $^3$H-thymidine incorporation was measured by scintillation counting and proliferative responses were expressed as the CPM (counts per minute) of triplicate wells. The data was shown in FIGS. 11 and 12.

Figure 11:
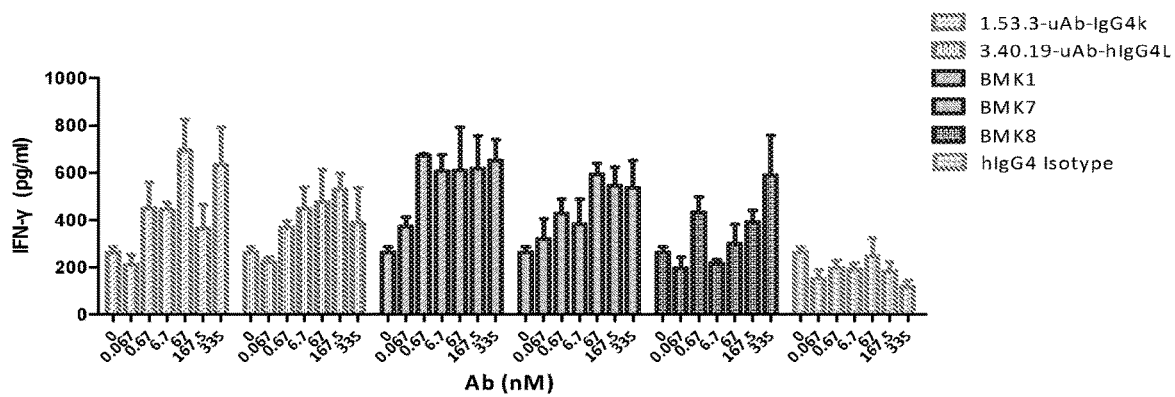
FIG. 11 shows the effects of human LAG-3 antibodies on human allogeneic mixed lymphocyte reaction, as measured by ELISA and reflected by the level of IFN-γ (ng/mL).
Figure 12:
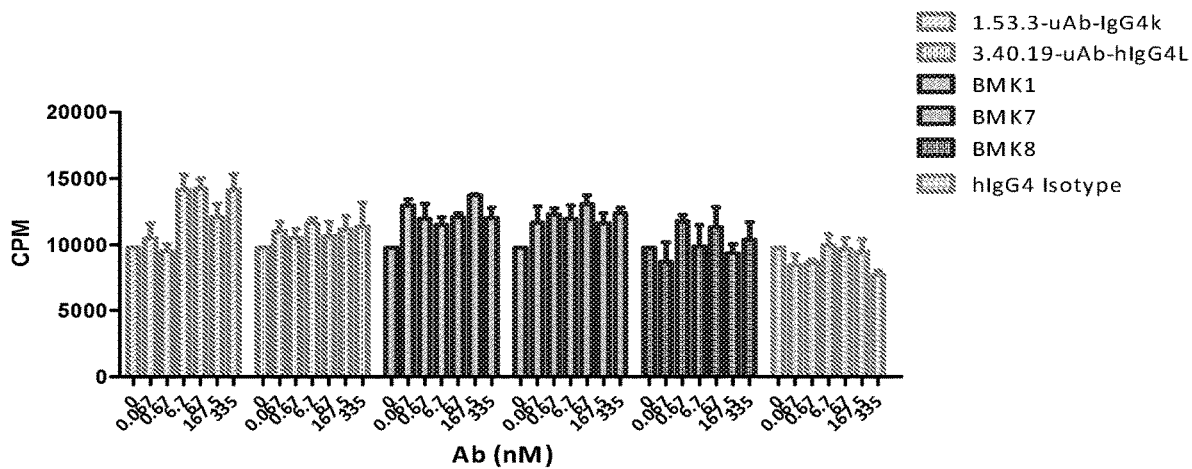
FIG. 12 shows the effects of human LAG-3 antibodies on human allogeneic mixed lymphocyte reaction, as measured by $^3$H-thymidine incorporation and reflected by proliferative responses which are expressed as the CPM (counts per minute) of triplicate wells.

As demonstrated in FIG. 11, LAG-3 antibodies of the disclosure "1.53.3-uAb-IgG4k" and "3.40.19-uAb-IgG4L" enhanced IFN-γ secretion in mixed lymphocyte reaction. Further, as shown in FIG. 12, LAG-3 antibodies of the disclosure "1.53.3-uAb-IgG4k" and "3.40.19-uAb-IgG4L" enhanced T cell proliferation in mixed lymphocyte reaction.

Example 12

ADCC and CDC Tests

In order to assess their ability to trigger Fc effector function, the anti-LAG-3 antibodies were evaluated whether they could mediate antibody-dependent cellular cell-mediated cytotoxicity (ADCC) and complement-dependent cytotoxicity (CDC) activity.

ADCC Test

Human LAG-3-expressing Flp-In-293 cells and various concentrations of LAG-3 antibodies were pre-incubated in 96-well round-bottom plate for 30 minutes; and then PBMCs, as effector, were added with the effector/target ratio of 50:1. The plate was kept at 37° C., 5% $CO_2$ for 4 hours. Target cell lysis was determined by LDH-based Cytotoxicity Detection Kit. The absorbance at 492 nm was read using a microplate reader. Herceptin and HER2-expressing cell line SK-Br-3 were used as positive control.

CDC test

Human LAG-3-expressing Flp-In-293, as target, and various concentrations of LAG-3 antibodies were mixed in 96-well round-bottom plate. Human complement was added at a final dilution of 1:50. The plate was kept at 37° C., 5% $CO_2$ for 2 hours. Target cell lysis was determined by CellTiter-Glo. The luminescence was read using a microplate reader. Rituximab and CD20-expressing cell line Raji was used as positive control.

Figure 13A:
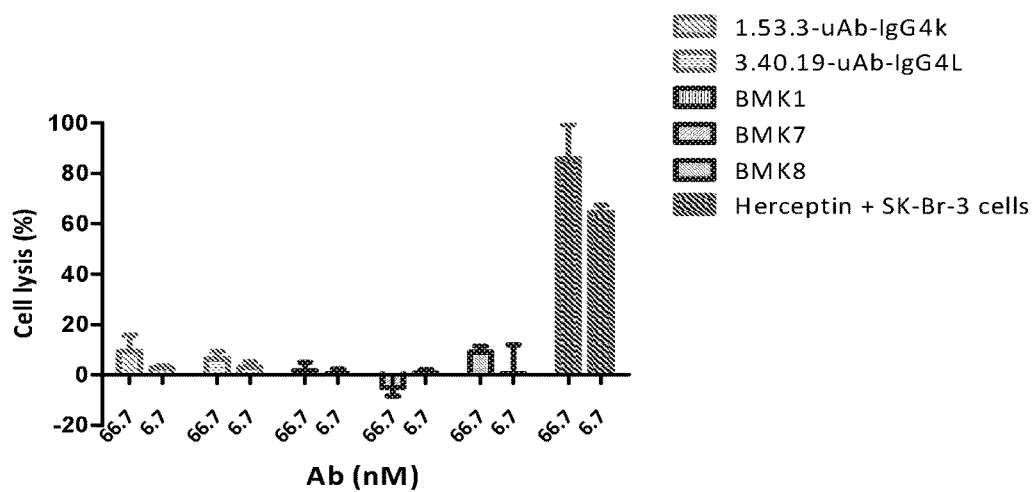
FIG. 13A-B shows the results of CDC test and ADCC test, by determining target cell lysis.
Figure 13B:
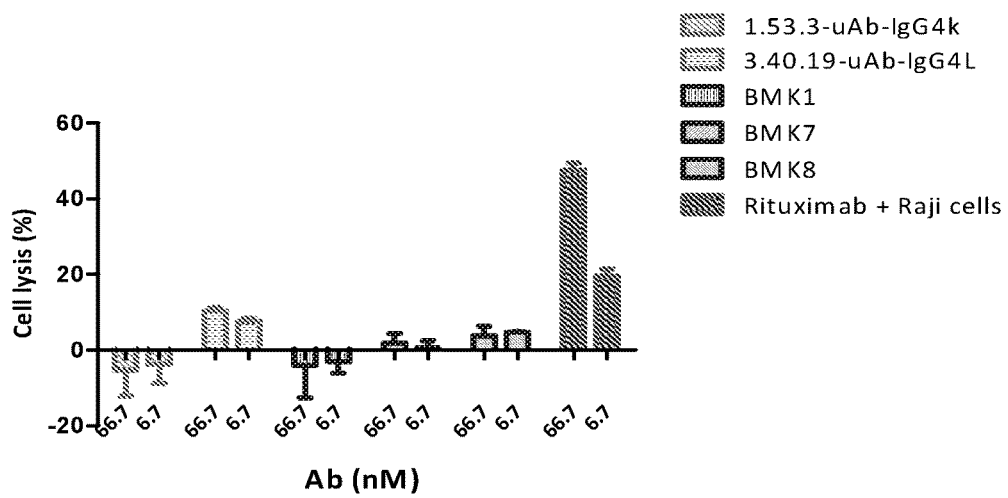

The data for ADCC test and CDC test were shown in FIGS. 13A and 13B. It is demonstrated that, LAG-3 antibodies of the disclosure, as represented by 1.53.3-uAb-IgG4k and 3.40.19-uAb-IgG4L, did not mediate ADCC (FIG. 13A) and CDC (FIG. 13B) effects.

Example 13

Serum Stability Test

Figure 14A:
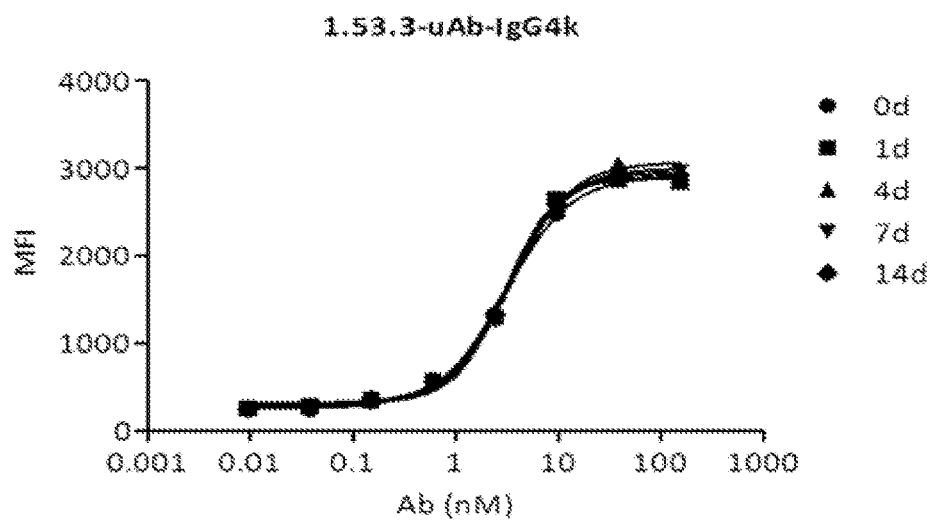
FIG. 14A-B shows the results of serum stability test, as measured by FACS and expressed by MFI of the cells.
Figure 14B:
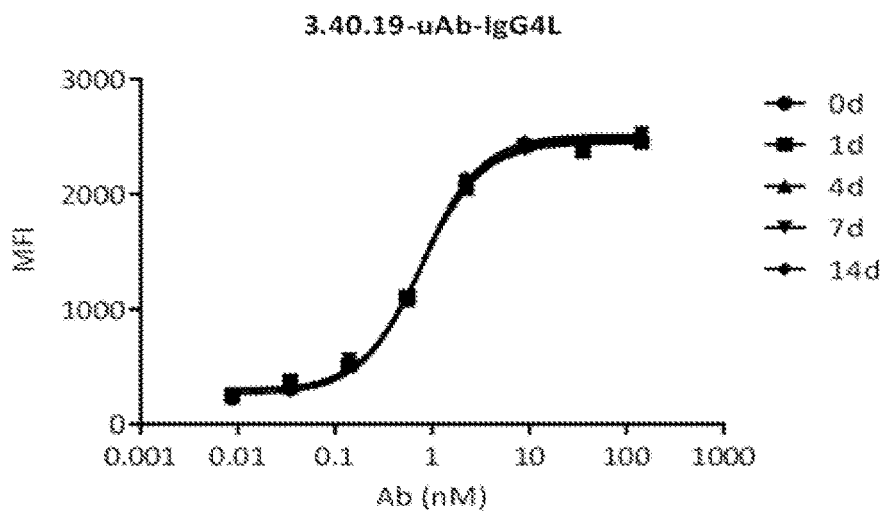

The lead Abs were incubated in freshly isolated human serum (serum content >95%) at 37° C. On indicated time points, an aliquot of serum treated sample was removed from the incubator and snap frozen in liquid $N_2$, and then stored at −80° C. until ready for test. The samples were quickly thawed immediately prior to the stability test. Human LAG-3 transfectant cells were incubated with various concentrations of lead antibodies at 4° C. for 1 hour. PE-labeled goat anti-human IgG was used to detect the binding of lead antibodies onto the cells. MFI of the cells was measured by a flow cytometer (BD FACSCanto II) and analyzed by FlowJo. The data was shown in FIGS. 14A and 14B.

It is demonstrated that the LAG-3 antibodies of the disclosure, as represented by 1.53.3-uAb-IgG4k and 3.40.19-uAb-IgG4L, were stable in fresh human serum for up to 14 days.

Those skilled in the art will further appreciate that the present invention may be embodied in other specific forms without departing from the spirit or central attributes thereof. In that the foregoing description of the present application discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An isolated antibody or the antigen-binding portion thereof that is capable of binding LAG-3, wherein the antibody or the antigen-binding portion thereof comprises:
   (a) a heavy chain variable region comprising the amino acid sequence of SEQ ID NO: 13; and a light chain variable region comprising the amino acid sequence of SEQ ID NO: 14; or
   (b) a heavy chain variable region comprising the amino acid sequence of SEQ ID NO: 15; and a light chain variable region comprising the amino acid sequence of SEQ ID NO: 16.

2. The isolated antibody or the antigen-binding portion thereof of claim 1, wherein the antibody or the antigen-binding portion thereof comprises:
   (a) a CDRH1, a CDRH2 and a CDRH3 of a VH sequence as set forth in SEQ ID NO: 13, and a CDRL1, a CDRL2 and a CDRL3 of a VL sequence as set forth in SEQ ID NO: 14; or
   (b) a CDRH1, a CDRH2 and a CDRH3 of a VH sequence as set forth in SEQ ID NO: 15, and a CDRL1, a CDRL2 and a CDRL3 of a VL sequence as set forth in SEQ ID NO: 16.

3. The isolated antibody or the antigen-binding portion thereof of claim 1, wherein the antibody or the antigen-binding portion thereof comprises:
   (a) a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a CDRL1 comprising the amino acid sequence of SEQ ID NO: 4, a CDRL2 comprising the amino acid sequence of SEQ ID NO: 5, and a CDRL3 comprising the amino acid sequence of SEQ ID NO: 6; or
   (b) a CDRH1 comprising the amino acid sequence of SEQ ID NO: 7, a CDRH2 comprising the amino acid sequence of SEQ ID NO: 8, a CDRH3 comprising the amino acid sequence of SEQ ID NO: 9, a CDRL1 comprising the amino acid sequence of SEQ ID NO: 10, a CDRL2 comprising the amino acid sequence of SEQ ID NO: 11, and a CDRL3 comprising the amino acid sequence of SEQ ID NO: 12.

4. The isolated antibody or the antigen-binding portion thereof of claim 1, wherein the isolated antibody or the antigen-binding portion thereof comprises:
   (a) a CDRH1 consisting of SEQ ID NO: 1;
   (b) a CDRH2 consisting of SEQ ID NO: 2;
   (c) a CDRH3 consisting of SEQ ID NO: 3;
   (d) a CDRL1 consisting of SEQ ID NO: 4;
   (e) a CDRL2 consisting of SEQ ID NO: 5; and
   (f) a CDRL3 consisting of SEQ ID NO: 6.

5. The isolated antibody or the antigen-binding portion thereof of claim 1, wherein the isolated antibody or the antigen-binding portion thereof comprises:
 (a) a CDRH1 consisting of SEQ ID NO: 7;
 (b) a CDRH2 consisting of SEQ ID NO: 8;
 (c) a CDRH3 consisting of SEQ ID NO: 9;
 (d) a CDRL1 consisting of SEQ ID NO: 10;
 (e) a CDRL2 consisting of SEQ ID NO: 11; and
 (f) a CDRL3 consisting of SEQ ID NO: 12.

6. The isolated antibody or the antigen-binding portion thereof of claim 1, having one or more of the following properties:
 (a) inhibits binding of LAG-3 to major histocompatibility (MHC) class II molecules;
 (b) inhibits binding of LAG-3 to fibrinogen-like protein 1 (FGL1) ligand molecules;
 (c) inhibits binding of LAG-3 to LSECtin and/or Galectin-3;
 (d) binds to human LAG-3 without cross-family reactions; or
 (e) has no cross-reactivity to human CD4.

7. The isolated antibody or the antigen-binding portion thereof of claim 1, wherein the antibody is a chimeric antibody, a humanized antibody or a fully human antibody.

8. The isolated antibody or the antigen-binding portion thereof of claim 7, wherein the antibody is a fully human monoclonal antibody produced by a rat having recombinant immunoglobulin loci.

9. A pharmaceutical composition comprising at least one antibody or antigen-binding portion thereof as defined in claim 1 and a pharmaceutically acceptable carrier.

10. A kit comprising a container comprising the antibody or antigen-binding portion thereof as defined in claim 1.

11. An isolated nucleic acid molecule, comprising a nucleic acid sequence encoding the heavy chain variable region and/or the light chain variable region of the isolated antibody as defined in claim 1.

12. An expression vector comprising the nucleic acid molecule of claim 11.

13. A host cell comprising the expression vector of claim 12.

14. A method for preparing an antibody or antigen-binding fragment thereof that binds to LAG-3, the method comprising:
 incubating the host cell of claim 13 in conditions suitable for expression the antibody or antigen-binding fragment thereof; and
 isolating the antibody or antigen-binding fragment thereof.

15. A method for inhibiting or blocking the binding of LAG-3 to LSECtin and/or Galectin-3, comprising in the presence of LAG-3 contacting LSECtin and/or Galectin-3 with the antibody or antigen-binding portion thereof as defined in claim 1.

16. A method for inhibiting growth of tumor cells in a subject, comprising administering to the subject the antibody or antigen-binding portion thereof as defined in claim 1 such that growth of the tumor is inhibited in the subject.

17. A method for treating cancers in a subject, comprising administering an effective amount of the antibody or antigen-binding portion thereof as defined in claim 1 to the subject.

18. A method for detecting LAG-3 in a sample, comprising contacting the sample with the antibody or antigen-binding portion thereof as defined in claim 1, and detecting presence or absence, or level of association, of the antibody bound in the sample.

* * * * *